(12) United States Patent
Day et al.

(10) Patent No.: US 12,398,419 B2
(45) Date of Patent: Aug. 26, 2025

(54) AUTOMATED RNA DETECTION USING LABELED 2'-O-METHYL RNA OLIGONUCLEOTIDE PROBES AND SIGNAL AMPLIFICATION SYSTEMS

(71) Applicant: Ventana Medical Systems, Inc., Tucson, AZ (US)

(72) Inventors: William Day, Tucson, AZ (US); Michael Farrell, Tucson, AZ (US); Zeyu Jiang, Tucson, AZ (US); Anne Pedata, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 1210 days.

(21) Appl. No.: 17/193,269

(22) Filed: Mar. 5, 2021

(65) Prior Publication Data

US 2021/0198728 A1    Jul. 1, 2021

Related U.S. Application Data

(60) Division of application No. 15/245,126, filed on Aug. 23, 2016, now Pat. No. 10,982,269, which is a continuation of application No. PCT/EP2015/053644, filed on Feb. 20, 2015.

(60) Provisional application No. 62/102,184, filed on Jan. 12, 2015, provisional application No. 61/943,933, filed on Feb. 24, 2014.

(51) Int. Cl.
| | |
|---|---|
| *C12Q 1/6841* | (2018.01) |
| *C12Q 1/6804* | (2018.01) |
| *C12Q 1/6816* | (2018.01) |
| *C12Q 1/682* | (2018.01) |
| *C12Q 1/6886* | (2018.01) |

(52) U.S. Cl.
CPC ......... *C12Q 1/6841* (2013.01); *C12Q 1/6804* (2013.01); *C12Q 1/6816* (2013.01); *C12Q 1/682* (2013.01); *C12Q 1/6886* (2013.01); *C12Q 2600/178* (2013.01)

(58) Field of Classification Search
CPC ...... C12Q 1/68; C12Q 1/6816; C12Q 1/6841; C12Q 2600/178
See application file for complete search history.

(56) References Cited

U.S. PATENT DOCUMENTS

| | | | |
|---|---|---|---|
| 10,041,950 B2 | 8/2018 | Alexander | |
| 10,982,269 B2* | 4/2021 | Farrell | C12Q 1/6816 |
| 2008/0268462 A1* | 10/2008 | Kosmeder | C07D 493/04 435/7.1 |
| 2012/0301886 A1* | 11/2012 | Farrell | C12Q 1/6816 977/774 |
| 2018/0328932 A1* | 11/2018 | Alexander | G01N 33/542 |

FOREIGN PATENT DOCUMENTS

WO        2013/148498 A1    10/2013

OTHER PUBLICATIONS

Sϕe et al., A sensitive alternative for microRNA in situ hybridizations using probes of 2'-O-methyl RNA+ LNA. J. of Histochemistry and Cytochemistry 59(7) :661-672 (Year: 2011).*
Wang et al., RNAscope: a novel in situ RNA analysis platform for formalin-fixed, paraffin-embedded tissues. J. of Molecular Diagnostics 14(1) :22-29 (Year: 2012).*
Majlessi et al., Advantages of 2'-O-methyl oligoribonucleotide probes for detecting RNA targets. Nucleic Acids Research 26(9) : 2224 (Year: 1998).*
Kierzek, et al., "The influence of locked nucleic acid residues on the thermodynamic properties of 2'-O-methyl RNA/RNA heteroduplexes," Nucleic Acids Research 33(16):5082-5093 (2005).
Bartel D. P., MicroRNAs: Target Recognition and Regulatory Functions, Cell, (2009), pp. 215-219, vol. 136.
Adachi, M. et al., "Identification of marine algicidal *Flavobacterium* sp. 5 N-3 using multiple probes and whole-cell hybridization", Fisheries Science, 2002, 713-720, 68.
Bottari, B. et al., Application of FISH technology for microbiological analysis: current state and prospects, Appl Microbiol Biotechnol, Oct. 19, 2006, 485-494, 73 (3).
De Block, M. et al., RNA-RNA in Hybridization Using Digoxigenin-Labeled Probes: The Use of High-Molecular-Weight Polyvinyl Alcohol in the Alkaline Phosphatase Indoxyl-Nitroblue Tetrazolium Reaction, Analytical Biochemistry, Nov. 15, 1993, 86-89, 215(1).
IPEA, International Preliminary Report on Patentability, International Preliminary Report on Patentability, Sep. 16, 2016, 1-13, N/A, WO.
ISA, International Search Report & Written Opinion, International Search Report & Written Opinion, Jul. 17, 2015, 1-18, N/A, WO.
Lee, Sanghoon et al., Use of multiple 16S rRNA-targeted fluorescent probes to increase signal strength and measure cellular RNA from natural planktonio bacteria, Marine Ecology Progress Series, Nov. 4, 1993, 193-201, 101.
Soe, M.J. et al., "A Sensitive Alternative for MicroRNA In Situ Hybridizations Using Probes of 2'-O-Methyl RNA + LNA", Journal of Histochemistry & Cytochemistry, 2011, 661-672, 59 (7).
Soe, M.J. et al., "Detection of Small Noncoding RNAs by In Situ Hybridization Using Probes of 2'-O-Methyl RNA + LNA", Methods in Molecular Biology, Jan. 1, 2014, 113-121, 1173, Humana Press, Inc.

* cited by examiner

*Primary Examiner* — Ethan C Whisenant
(74) *Attorney, Agent, or Firm* — Charney IP Law LLC; Thomas M. Finetti

(57) ABSTRACT

Disclosed herein are methods and compositions for detecting differential expression of certain miRNAs in cancer cells or their surrounding normal tissues in the tumor microenvironment. The disclosure describes an automated, highly sensitive and specific method for detection of any cellular RNA molecule, including microRNA, messenger RNA and non-coding RNA. The technology includes probe design as well as probe use in an automated fashion for detection of RNA molecules in formalin-fixed paraffin-embedded tissue (FFPET) samples.

21 Claims, 9 Drawing Sheets
(8 of 9 Drawing Sheet(s) Filed in Color)

AUTOMATED RNA DETECTION USING LABELED 2'-O-METHYL RNA OLIGONUCLEOTIDE PROBES AND SIGNAL AMPLIFICATION SYSTEMS

CROSS-REFERENCE TO RELATED APPLICATIONS

This patent application is a divisional of U.S. patent application Ser. No. 15/245,126, filed Aug. 23, 2016, which is a continuation of International Patent Application No. PCT/EP2015/053644, filed Feb. 20, 2015, which claims priority to and the benefit of U.S. Provisional Patent Application No. 62/102,184, filed Jan. 12, 2015, and U.S. Provisional Patent Application No. 61/943,933, filed Feb. 24, 2014. Each patent application is incorporated herein by reference in its entirety.

FIELD

This disclosure relates to an automated, highly sensitive and specific method for detection of any cellular RNA molecule, including microRNA, messenger RNA and non-coding RNA. The technology includes probe design as well as probe use in an automated fashion for detection of RNA molecules in formalin-fixed paraffin-embedded tissue (FFPET) samples.

BACKGROUND

The human genome encodes more than one thousand short (17-24 base) non-coding microRNA molecules that regulate diverse cellular functions. Several of these functions are known to be involved in tumorigenesis including cell growth, motility, and immune surveillance. Not surprisingly, numerous clinical studies suggest that many microRNAs will serve as potent prognostic and/or predictive biomarkers for a variety of diseases including breast, colorectal, lung, and prostate cancers. However, due to their short sequence length, technical obstacles exist for detection of these potential biomarker targets: (i) limited target sequence limits probe length and subsequent target specificity as well as (ii) detection sensitivity since short probes require significant amplification technologies to generate a visible signal; lastly, (iii) short microRNA targets may be less stable in tissue (increased ribonuclease sensitivity and/or limited crosslinking to cellular components).

MicroRNAs regulate protein expression mainly by inhibiting translation and/or promoting mRNA degradation (Lin He & Gregory J. Hannon Nat. Rev. Genetics 5, 522-531). Over 50% of mRNAs are estimated to be regulated by one or more miRNAs and a single miRNA may regulate several to dozens of genes, miRNAs have been demonstrated to function in many physiological and pathological processes. miRNAs can function as tumor suppressors or oncogenes (Esquela-Kerscher et al. Nat. Rev. Cancer 6, 259-269.).

There are several RNA detection technologies commercially available. Ventana Medical Systems, Inc. has products for automated kappa (Kappa DNP Probe Catalog #: 495-524) and lambda (Lambda DNP Probe Catalog #: 664-693) light chain mRNA expression in FFPET, with commercially available detection chemistries (ISH iVIEW Blue Plus Detection Kit Catalog #: 760-097). This technology does not use 2'-O-methyl RNA oligonucleotide probes or amplification (e.g. tyramide signal amplification). Advanced Cell Diagnostics (ACD) has a full line of products for manual detection of mRNA with their RNAScope technology. Extensive amplification, mediated through branched-DNA technology, post hybridization, is used to amplify the signal sufficiently for detection. Both chromogenic in situ hybridization (CISH) and fluorescence in situ hybridization (FISH) detections following branched-DNA amplification are offered by ACD. This technology is mainly used manually with limited partial automation provided by the Ventana Discovery instrument. A substantial limitation, overcome by the presently disclosed technology, is that it requires a minimum of 300 bases of RNA target length; therefore, the ACD technology is not capable of detecting microRNA targets. Exiqon provides locked nucleic acid oligonucleotide probes for microRNA detection: the technology is limited to probe design and synthesis and does not provide any specific manual or automated detection capabilities (chromogen or fluorophore development or deposition).

SUMMARY

This disclosure describes a novel, highly sensitive, and fully automated assay for in-situ detection of all RNA species, including messenger RNA of secretory factors, non-coding RNA, and microRNA in tissues, in particular formalin-fixed paraffin-embedded tissue (FFPET). It was discovered that 2'-O-methyl modified RNA oligonucleotides labelled with detectable moieties (e.g., haptens) could be used as probes for in-situ hybridization to RNA target molecules. It was discovered that the probes possess increased in situ binding affinity to target RNA molecules compared to DNA probes, RNA oligonucleotide probes, or riboprobes: thus providing increased assay sensitivity. Furthermore, it was discovered that 2'-O-methyl modified RNA oligonucleotides have superior nuclease resistance than RNA probes or even DNA probes in the context of tissue staining.

As such, two benefits conferred by the new technology are that 2'-O-methyl RNA oligonucleotide probes have higher affinity to RNA targets than DNA or RNA probes and the methyl group confers resistance to RNases and other ribonucleases. In particular examples, probes for miRNA were developed. In some embodiments, each miRNA probe is labeled with two haptens: either synthesized directly (DNP) or using amine modification then haptenized NHS.

The present technology seeks to enable a robust and efficient tool to probe the differential expression of certain miRNAs in cancer cells or their surrounding normal tissues in the tumor microenvironment. In so enabling this tool, the present technology is enabled as an effective tool for the diagnosis and treatment of cancer.

In the current disclosure, new RNA detection technologies, which include modified RNA oligonucleotide probes and sensitive tyramide-hapten/Silver detection designed for detection of longer RNA targets, were adopted for automated detection of microRNA targets in formalin-fixed paraffin embedded (FFPE) tissue.

In illustrative embodiments, a method for detecting a target RNA in a tissue sample is disclosed. The method comprises contacting the sample with an antigen retrieval reagent: contacting the sample with a labeled synthetic 2'-O-methyl oligonucleotide probe under conditions sufficient that the probe hybridizes to the target RNA in the sample; rinsing the sample so as to remove unbound probe; contacting the sample with an amplification labels reagent so as to deposit a plurality of amplification labels proximally to the target RNA; contacting the sample with a detection reagent so as to deposit a detectable label proximally to the target RNA; detecting the target RNA by visualizing the detectable label. In one embodiment, the labeled synthetic 2'-O-methyl oligonucleotide probe is between about 20 and about 200, between about 20 and about 100 nucleotides in length. In another embodiment, the method uses conditions that preserve cell morphology.

Also disclosed are kits including one or more of the probes or probe sets disclosed herein. Optionally a kit may comprise additional reagents, e.g., signal amplification reagents (e.g., reactive chromogen conjugate system reagents).

The methods of the present invention may allow for the detection of more than one (e.g., 2, 3, 4, etc.) different targets. In some embodiments, different detectable labels and/or detection systems may be used for each of the targets such that each can be individually detected in a single sample. Any appropriate detectable label and/or detection system may be used.

More specifically, the present invention features systems for bright field in situ hybridization. In some embodiments, the system comprises a probe set comprising X unique 2'-O-methyl RNA probes specific to a target RNA, wherein X≥2 (e.g., X=2, X=3, X=4, X=5, etc.), the probes target X distinct portions within the target RNA. Each 2'-O-methyl RNA probe may be conjugated with at least one detectable moiety. The detectable moiety may be adapted to bind a reactive chromogen conjugate system (e.g. tyramide chromogen conjugate system) for signal amplification. In some embodiments, the 2'-O-methyl RNA probes each comprise between 15 to 30 nucleotides, between 20 to 50 nucleotides, between 40 to 80 nucleotides, between 20 to 100 nucleotides, or between 20 to 200 nucleotides in length.

In some embodiments, the 2'-O-methyl RNA probes are each conjugated with at least two detectable moieties, at least three detectable moieties, at least four detectable moieties, or at least five detectable moieties. In some embodiments, the detectable moiety comprises a hapten. In some embodiments, the hapten comprises dinitrophenol (DNP). In some embodiments, the reactive chromogen conjugate system comprises a tyramide-hapten conjugate, or any other appropriate conjugate system. In some embodiments, the probes each comprise at least one detectable moiety per 20 base pairs of the probe.

In some embodiments, the system further comprises a means of making the target microRNA visible. In some embodiments, the means of making the target microRNA visible comprises the step of contacting the probes with the reactive chromogen conjugate system specific to the detectable moieties of the probes, the reactive chromogen conjugate system emits a color. In some embodiments, the system further comprises a means of visualizing the target microRNA, wherein the detectable moieties are made visible by the reactive chromogen conjugate system, the visibility of the detectable moieties is indicative of the target microRNA. In some embodiments, the means of visualizing the target microRNA comprises a bright field microscope.

The present invention also features a system for bright field in situ detection of a microRNA target. In some embodiments, the system comprises a target probe comprising a unique 2-O-methyl RNA probe specific to the target microRNA, wherein the 2'-O-methyl RNA probe is conjugated with at least one detectable moiety disposed at either the 3' end or the 5' end of the probe; and a reactive chromogen conjugate system effective for signal amplification, the reactive chromogen conjugate system is adapted to bind to the detectable moiety of the target probe.

In some embodiments, the 2'-O-methyl RNA probe comprises between 15 to 30 nucleotides. In some embodiments, the probe comprises a first detectable moiety disposed at the 3' end of the probe and a second detectable moiety disposed at the 5' end of the probe. In some embodiments, the detectable moiety comprises a hapten. In some embodiments, the hapten comprises dinitrophenol (DNP). In some embodiments, the reactive chromogen conjugate system comprises a tyramide-hapten conjugate.

In some embodiments, the system further comprises a means of making the target microRNA visible. In some embodiments, the means of making the target microRNA visible comprises the step of contacting the probes with the reactive chromogen conjugate system specific to the detectable moieties of the probes, the reactive chromogen conjugate system emits a color. In some embodiments, the system further comprises a means of visualizing the target microRNA, wherein the detectable moieties are made visible by the reactive chromogen conjugate system, the visibility of the detectable moieties is indicative of the target microRNA. In some embodiments, the means of visualizing the target microRNA comprises a bright field microscope.

The present invention also features a slide comprising it plurality of cells chromogenically stained for a target RNA, wherein the slide is made using a system as disclosed herein (e.g., target probe comprising a unique 2'-O-methyl RNA probe specific to the target microRNA, probe set of unique 2'-O-methyl RNA probes, etc.).

The present invention also features methods of bright field in situ hybridization. In some embodiments, the method comprises contacting a sample with an antigen retrieval reagent; contacting the sample with a probe or probe set as disclosed herein under conditions sufficient that the probe hybridizes to the target RNA in the sample; rinsing the sample to remove unbound probe: and detecting the target RNA by making visible the detectable moiety.

In some embodiments, the method comprises contacting a sample with a probe set specific for a target RNA under conditions sufficient that the probe set hybridizes to the target RNA in the sample, the probe set comprises X unique 2'-O-methyl RNA probes, wherein X≥2, the 2'-O-methyl RNA probes target X distinct portions within the target RNA, wherein each 2'-O-methyl RNA probe is conjugated with at least one hapten; contacting the sample with a first anti-hapten antibody conjugated with a first enzyme, the first anti-hapten antibody is specific for the X unique RNA probes; contacting the sample with a reactive chromogen conjugate system (e.g., tyramide-hapten conjugate or any other appropriate conjugate), wherein the first enzyme of the first anti-hapten antibody binds the reactive chromogen conjugate system to the first anti-hapten antibody (a tyramide hapten conjugate also binds to tissue); contacting the sample with a second anti-hapten antibody conjugated with a second enzyme, the second anti-hapten antibody is specific for the reactive chromogen conjugate system, the second enzyme catalyzes visibility of the chromogen: wherein visibility of the chromogen is indicative of the target RNA.

In some embodiments, the method comprises contacting a sample with a 2'-O-methyl RNA probe specific for a target RNA under conditions sufficient that the 2'-O-methyl RNA probe hybridizes to the target RNA in the sample, the 2'-O-methyl RNA probe is conjugated with at least one hapten, and is between 15 to 30 nucleotides in length; contacting the sample with a first anti-hapten antibody conjugated with a first enzyme, the first anti-hapten antibody is specific for the 2'-O-methyl RNA probe; contacting the sample with a reactive chromogen conjugate system (e.g., tyramide-hapten conjugate or any other appropriate conjugate), the first enzyme of the first anti-hapten antibody binds the active chromogen conjugate system to the first anti-hapten antibody; contacting the sample with a second anti-hapten antibody conjugated with a second enzyme, the second anti-hapten antibody is specific for the active chromogen conjugate system, the second enzyme catalyzes visibility of the chromogen; wherein visibility of the chromogen is indicative of the target RNA.

In some embodiments, the 2'-O-methyl RNA probe is conjugated with two haptens. In some embodiments, the hapten comprises dinitrophenol (DNP). In some embodiments, a first hapten is located at a 3' end of the probe, and a second hapten is located at a 5' end of the probe.

In some embodiments, the method comprises fixation utilizing the 2+2 system as described in U.S. patent application Ser. No. 13/372,040, published as US 20120214195 ('195), filed Feb. 13, 2012, assigned to Ventana Medical Systems, Inc. the content of which is incorporated herein in its entirety.

See FIGS. 5-9, which detail the impact of fixation on staining e.g., MCF-7 xenograft tissues. The data detailed in FIGS. 5-9 show the impact at room temperature and various other temperatures utilizing the 2+2 methods as described and claimed in the '195 patent application. Briefly, the general method as disclosed in the '195 patent application proposes a method for aldehyde fixation, exemplified by formalin fixation, of a tissue sample, comprising applying, immersing or otherwise contacting an aldehyde solution and a tissue sample for a first time period and at a first temperature, and then raising the temperature of the tissue sample to a second temperature higher than the first temperature for a second time period.

As detailed in the '195 patent application and applied herein, generally the tissue sample second temperature is higher than the first temperature. The raising of the tissue sample temperature may comprise raising the temperature of the tissue sample quickly or even abruptly to the second temperature. The raising of the sample temperature is done to increase cross-linking while still preserving the underlying sample reactivity. Alternatively, the raising of the tissue sample to the second temperature may be accomplished by immersing the tissue sample in a solution at the second temperature, wherein the solution can be the same or a different aldehyde solution. The second temperature typically is greater than ambient, more typically is greater than about 22 degrees Celsius, even more typically is from greater than about 22 degrees Celsius to at least about 50 degrees Celsius, and even more typically is from greater than about 22 degrees Celsius to about 45 degrees Celsius. The second time period is effective to allow substantially complete cross-linking of endogenous molecules and structures to occur. While the second time period may vary, it typically ranges from greater than 15 minutes up to at least about 5 hours, typically is from about 1 hour to about 4 hours, and even more typically is from about 2 hours to about 3 hours. The speed and methods used for raising the temperatures are so designed that optimal preservation of biomolecules prone to degradation such as microRNA/RNA and post-translation modifications is achieved. Refer to the '195 patent application.

While the first time period may vary depending on tissue thickness, for ASCO CAP guidelines of up to 4 mm thickness, it typically ranges from about 15 minutes up to about 4 hours, more typically from greater than 15 minutes to about 3 hours, and even more typically is from about 1 hour to about 2 hours. It is recognized that for thicker samples, the first time period will be dictated by diffusion rate. The first temperature is from at least −20 degrees Celsius to about 15 degrees Celsius, typically is from at least 0 degrees Celsius to about 15 degrees Celsius, more typically at least 0 degrees Celsius to about 10 degrees Celsius, and even more typically from about 3 degrees Celsius to about 5 degrees Celsius.

Certain embodiments of the method disclosed in the '195 patent application comprise applying a first aldehyde solution at a first temperature to the tissue sample, followed by applying a second aldehyde solution to the tissue sample. The second aldehyde solution may be different from the first aldehyde solution. For example, the solutions can be at different concentrations, or the second aldehyde solution may comprise an aldehyde different from the first aldehyde. The aldehyde typically is a lower alkyl aldehyde, such as formaldehyde, glutaraldehyde, or combinations thereof.

As noted in the '195 application, the 2+2 method offers at least three improvements over existing methods in the art. First, by allowing formalin to penetrate into the tissue section in a cold environment can significantly reduce enzyme activities. Second, by increasing the cross-linking kinetics by quickly raising the tissue sample temperature, the cellular constituents are "locked" into place more rapidly than what would be observed at room temperature. This combination makes this technique superior over existing methods and for the first time allows modification states to be preserved in FFPE tissues. Third, this represents a general method believed to be applicable to a wide variety of modification states and enzymes. While other methods target a specific set of modification enzymes, this method rapidly disables all modification enzymes and therefore preserve the general cellular status much better than gold standard room temperature procedures. The teaching in the '195 patent continues that i. Since the invention is not limited to a specific set of biomolecules or biomolecules containing specific post-translations modifications, it is believed that this method represents a general method for preservation of any biomolecule or modification state. Thus, this invention can preserve with high quality quantities of biomolecules and biomolecules containing specific post-translations modifications. (paragraph 0021)

As a consequence, it is believed that the same benefits attend the method of the present invention.

The foregoing and other features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

I. Terms

Figure 1:
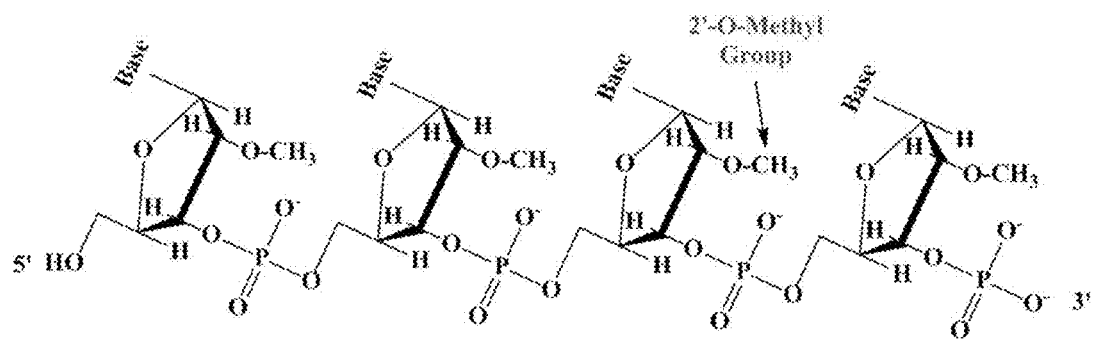
FIG. 1 shows an example of a structure of a 2'-O'Methyl RNA oligonucleotide.

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including" Hence "comprising A or B" means "including A" or "including B" or "including A and B."

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et at, Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology. Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999: Harlow and Lane, Antibodies: A Laboratory Manual. Cold Spring Harbor Laboratory Press, 1990: and Harlow and Lane, Using Antibodies: A Laboratory Manual. Cold Spring Harbor Laboratory Press, 1999, the disclosures of which are incorporated in their entirety by reference herein.

All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of the disclosure, the following explanations of specific terms are provided:

Antibody:

A polypeptide that includes at least a light chain or heavy chain immunoglobulin variable region and specifically binds an epitope of an antigen (such as CD79a protein). Antibodies include monoclonal antibodies, polyclonal antibodies, or fragments of antibodies. An antibody can be conjugated or otherwise labeled with a detectable label, such as an enzyme, hapten, or fluorophore.

Detectable Label (or Detectable Moiety):

A compound or composition that is conjugated directly or indirectly to another molecule (such as a nucleic acid probe) to facilitate detection of that molecule. Specific, non-limiting examples of labels include fluorescent and fluorogenic moieties, chromogenic moieties, haptens, affinity tags, and radioactive isotopes. The label can be directly detectable (e.g., optically detectable) or indirectly detectable (for example, via interaction with one or more additional molecules that are in turn detectable). Exemplary labels in the context of the probes disclosed herein are described below. Methods for labeling nucleic acids, and guidance in the choice of labels useful for various purposes, are discussed, e.g., in Sambrook and Russell, in Molecular Cloning: A Laboratory Manual, 3rd Ed., Cold Spring Harbor Laboratory Press (2001) and Ausubel et al., in Current Protocols in Molecular Biology, Greene Publishing Associates and Wiley-Intersciences (1987, and including updates).

Detectable labels may include chromogenic, fluorescent, phosphorescent and/or luminescent molecules, catalysts (such as enzymes) that convert one substance into another substance to provide a detectable signal (such as by converting a colorless substance into a colored substance or vice versa, or by producing a precipitate or increasing sample turbidity), haptens that can be detected through antibody-hapten binding interactions using additional detectably labeled antibody conjugates, and paramagnetic and magnetic molecules or materials. Particular examples of detectable labels include: enzymes, such as horseradish peroxidase, alkaline phosphatase, acid phosphatase, glucose oxidase, β-galactosidase or β-glucuronidase: fluorophores, such as fluoresceins, luminophores, coumarins, BODIPY dyes, resorufins, and rhodamines (many additional examples of fluorescent molecules can be found in The Handbook—A Guide to Fluorescent Probes and Labeling Technologies, Molecular Probes. Eugene, OR); nanoparticles, such as quantum dots (U.S. Pat. Nos. 6,815,064, 6,682,596 and 6,649,138, each of which is incorporated in its entirety by reference herein); metal chelates, such as DOTA and DPTA chelates of radioactive or paramagnetic metal ions like Gd3+; and liposomes, for example, liposomes containing trapped fluorescent molecules. Where the detectable label includes an enzyme, a detectable substrate such as a chromogen, a fluorogenic compound, or a luminogenic compound is used in combination with the enzyme to generate a detectable signal (a wide variety of such compounds are commercially available, for example, from Life Technologies, Carlsbad, CA).

Alternatively, an enzyme can be used in a metallographic detection scheme. In some examples, metallographic detection methods include using an enzyme, such as alkaline phosphatase, in combination with a water-soluble metal ion and a redox-inactive substrate of the enzyme. The substrate is converted to a redox-active agent by the enzyme, and the redox-active agent reduces the metal ion, causing it to form a detectable precipitate (see, for example, U.S. Pat. Nos. 7,642,064; 7,632,652: each of which is incorporated by reference herein). In other examples, metallographic detection methods include using an oxido-reductase enzyme (such as horseradish peroxidase) along with a water soluble metal ion, an oxidizing agent and a reducing agent, again to form a detectable precipitate (see, for example, U.S. Pat. No. 6,670,113, which is incorporated in its entirety by reference herein). Haptens are small molecules that can be bound by antibodies. Exemplary haptens include dinitrophenyl (DNP), biotin, digoxigenin (DIG), and fluorescein. Additional haptens include oxazole, pyrazole, thiazole, nitroaryl, benzofuran, triperpene, urea, thiourea, rotenoid, coumarin and cyclolignan haptens, such as those disclosed in U.S. Pat. No. 7,695,929, which is incorporated in its entirety by reference herein.

Hybridization:

To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. The presence of a chemical which decreases hybridization (such as formamide) in the hybridization buffer will also determine the stringency (Sadhu et al., J. Biosci. 6:817-821, 1984). Calculations regarding hybridization conditions for attaining particular degrees of stringency are discussed in Sambrook et al., (1989) Molecular Cloning, second edition, Cold Spring Harbor Laboratory, Plainview, NY (chapters 9 and 11). Hybridization conditions for ISH are also discussed in Landegent et al., Hum. Genet. 77:366-370, 1987; Lichter et al., Hum. Genet, 80:224-234, 1988; and Pinkel et al., Proc. NaI Acad. Sci. USA 85:9138-9142, 1988.

In Situ Hybridization (ISH):

A method of determining the presence or distribution of a nucleic acid in a sample using hybridization of a labeled nucleic acid probe to localize a specific DNA or RNA sequence in a portion or section of tissue (in situ), or, if the tissue is small enough (e.g., plant seeds, *Drosophila* embryos), in the entire tissue (whole mount ISH). DNA ISH can be used to determine the structure of chromosomes, such as for use in medical diagnostics to assess chromosomal integrity and/or to determine gene copy number in a sample. RNA ISH measures and localizes mRNAs and other transcripts within tissue sections or whole mounts.

For ISH, sample cells and tissues are usually treated to fix the target nucleic acids in place and to increase access of the probe to the target molecule. The detectably labeled probe hybridizes to the target sequence at elevated temperature, and then the excess probe is washed away. Solution parameters, such as temperature, salt and/or detergent concentration, can be manipulated to remove any non-identical interactions (e.g., so only exact sequence matches will remain bound). Then, the labeled probe is localized and potentially quantitated in the tissue using either autoradiography, fluorescence microscopy or immunohistochemistry, respectively. ISH can also use two or more probes, which are typically differently labeled to simultaneously detect two or more nucleic acids.

Isolated:

An "isolated" biological component (such as a nucleic acid molecule, protein, or cell) has been substantially separated or purified away from other biological components in a preparation, a cell of an organism, or the organism itself, in which the component occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins. In some examples, the nucleic acid probes disclosed herein are isolated nucleic acid probes.

Probe:

A nucleic acid molecule that is capable of hybridizing with a target nucleic acid molecule (e.g., genomic target nucleic acid molecule) and, when hybridized to the target, is capable of being detected either directly or indirectly. Thus probes permit the detection, and in some examples quantification, of a target nucleic acid molecule. In particular examples, a probe includes at least two segments complementary to uniquely specific nucleic acid sequences of a target nucleic acid molecule and are thus capable of specifically hybridizing to at least a portion of the target nucleic acid molecule. Generally, once at least one segment or portion of a segment has (and remains) hybridized to the target nucleic acid molecule other portions of the probe may (but need not) be physically constrained from hybridizing to those other portions' cognate binding sites in the target (e.g., such other portions are too far distant from their cognate binding sites): however, other nucleic acid molecules present in the probe can bind to one another, thus amplifying signal from the probe. A probe can be referred to as a "labeled nucleic acid probe," indicating that the probe is coupled directly or indirectly to a detectable moiety or "label," which renders the probe detectable.

Sample:

A specimen containing DNA (for example, genomic DNA), RNA (including mRNA), protein, or combinations thereof, obtained from a subject. Examples include, but are not limited to, chromosomal preparations, peripheral blood, urine, saliva, tissue biopsy, fine needle aspirate, surgical specimen, bone marrow, amniocentesis samples, and autopsy material. In one example, a sample includes genomic DNA. In some examples, the sample is a cytogenetic preparation, for example which can be placed on microscope slides, in particular examples, samples are used directly, or can be manipulated prior to use, for example, by fixing (e.g., using formalin).

Sequence Identity:

The identity (or similarity) between two or more nucleic acid sequences is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988: Higgins & Sharp, CABIOS 5:151-3, 1989; Corpet et al., Nuc Acids Res. 16:10881-90, 1988; Huang et al. Computer Appls, in the Biosciences 8:155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biotechnology and on the Internet, for use in connection with the sequence analysis programs blastp, blastn, blastx, tblastn and tblastx. Additional information can be found at the NCBI web site.

BLASTN may be used to compare nucleic acid sequences, while BLASTP may be used to compare amino acid sequences. If the two compared sequences share homology, then the designated output file will present those regions of homology as aligned sequences. If the two compared sequences do not share homology, then the designated output file will not present aligned sequences.

The BLAST-like alignment tool (BLAT) may also be used to compare nucleic acid sequences (Kent, Genome Res. 12:656-664, 2002). BLAT is available from several sources, including Kent Informatics (Santa Cruz, CA) and on the Internet (genome.ucsc.edu).

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 15 consecutive nucleotides from an identified sequence as follows contains a region that shares 75 percent sequence identity to that identified sequence (that is, 15+20*100=75).

Subject:

Any multi-cellular vertebrate organism, such as human or non-human mammals (e.g., veterinary subjects).

Target Nucleic Acid Sequence or Molecule:

A defined region or particular portion of a nucleic acid molecule, for example a portion of a genome (such as a gene or a region of mammalian genomic DNA containing a gene of interest). In an example where the target nucleic acid sequence is a target genomic sequence, such a target can be defined by its position on a chromosome (e.g., in a normal cell), for example, according to cytogenetic nomenclature by reference to a particular location on a chromosome; by reference to its location on a genetic map; by reference to a hypothetical or assembled contig; by its specific sequence or function: by its gene or protein name; or by any other means that uniquely identities it from among other genetic sequences of a genome. In some examples, the target nucleic acid sequence is mammalian genomic sequence (for example human genomic sequence).

In some examples, alterations of a target nucleic acid sequence (e.g., genomic nucleic acid sequence) are "associated with" a disease or condition. In some examples, detection of the target nucleic acid sequence can be used to infer the status of a sample with respect to the disease or condition. For example, the target nucleic acid sequence can exist in two (or more) distinguishable forms, such that a first form correlates with absence of a disease or condition and a second (or different) form correlates with the presence of the disease or condition. The two different forms can be qualitatively distinguishable, such as by polynucleotide polymorphisms, and/or the two different forms can be quantitatively distinguishable, such as by the number of copies of the target nucleic acid sequence that are present in a cell.

Uniquely Specific Sequence:

A nucleic acid sequence (for example, a sequence of at least of at least 20 bp (such as at least 20 bp, 30 bp, 40 bp, 50 bp, 60 bp, 70 bp, 80 bp, 90 bp, 100 bp, or more) that is present only one time in a haploid genome of an organism. Ina particular example, a uniquely specific nucleic acid sequence is a nucleic acid sequence from a target nucleic acid that has 100% sequence identity with the target nucleic acid and has no significant identity to any other nucleic acid sequences present in the specific haploid genome that includes the target nucleic acid.

Vector:

Any nucleic acid that acts as a carrier for other ("foreign") nucleic acid sequences that are not native to the vector. When introduced into an appropriate host cell a vector may replicate itself (and, thereby, the foreign nucleic acid sequence) or express at least a portion of the foreign nucleic acid sequence. In one context, a vector is a linear or circular nucleic acid into which a nucleic acid sequence of interest is introduced (for example, cloned) for the purpose of replication (e.g., production) and/or manipulation using standard recombinant nucleic acid techniques (e.g., restriction digestion). A vector can include nucleic acid sequences that permit it to replicate in a host cell, such as an origin of replication. A vector can also include one or more selectable marker genes and other genetic elements known in the art. Common vectors include, for example, plasmids, cosmids, phage, phagemids, artificial chromosomes (e.g., BAC, PAC, HAC, YAC), and hybrids that incorporate features of more than one of these types of vectors. Typically, a vector includes one or more unique restriction sites (and in some cases a multi-cloning site) to facilitate insertion of a target nucleic acid sequence.

II. Detailed Probe Design

2'-O-methyl RNA oligonucleotide (2'OMe) has a few desirable properties as probes for in situ detection of any RNA target in FFPE tissues: 1) 2'OMe probes have higher affinity to RNA than DNA or RNA probes; 2) 2'OMe probes are resistant to nucleases; 3) Coupling efficiency during chemical synthesis is higher than DNA, so the yield of full length product is higher. Referring now to FIG. 1, shown is au exemplary structure of a 2'-O-methyl RNA oligonucleotide as described herein. For mRNA and non-coding RNA targets, 80 nucleotide (nt) long 2'OMe probes were chosen to balance specificity and number of hapten per probe. Each 80 nt 2'OMe probe contains S haptens by incorporating one hapten every 20 nucleotide through the chemical synthesis. Although one 2'OMe probe can detect RNA targets, we empirically determined that using a mixture of three independent 2'OMe probes for one RNA target further increases detection sensitivity without sacrificing specificity. For each RNA target, six 2'OMe probes were select and synthesis was attempted. By selecting the best three of the six synthesized, lower yielding, lower sequence specificity, or other unforeseen problems could be mitigated. It was discovered that, for most targets, any three probes from the six could be used interchangeably. For certain RNA targets, only 2 or 3 80 nt probes are selected.

In order to effectively select a set of six probe for mRNA or non-coding RNA targets, a bioinformatics tool set was built to semi/automate the whole process. The bioinformatics tool takes either a sequence file or GenBank ID as one of the inputs, in the latter case, the software retrieves the sequence(s) from GenBank directly. The tool then runs a repeat database search to mask any repetitive sequences as these sequences are highly abundant in the genome. Without masking the repeats, the resultant probes would generate unwanted background (lack of specificity). The tool then generated all potential probes with predefined GC content and melting temperature ranges avoiding the masks by the repeat database search. In addition, the tool was used to take other inputs such as range in the sequence in case a specific region of RNA is targeted and output format etc. The tool again took all generated probes and performed a specialized BLASTN search designed for short oligonucleotides against local genomic, mRNA, and EST databases of interest, and based on the number of hits and associated BLAST bit score and e-value ('NSE'), a probe was selected or discarded. The remaining sequences were subjected to folding structural prediction analysis. The probes were folded with RNAfold, a leading open source RNA molecule folding software, and probes with hairpin structure or low $\Delta G$ (cutoff $-25$ kcal/mol) were excluded from further consideration. Six probes were selected for chemical synthesis from the remaining pool.

2'-O-methyl RNA oligonucleotides were synthesized with oligonucleotide synthesizer MerMade model 192. A set of 30 probes of 80 nt length take about 48 hours to finish. The scale of the synthesis was usually 50 nM, which produces probes enough for staining about 5 million slides of FFPET at the concentrations described herein.

The quality of synthesized 2-O-methyl RNA probes was one of the determining factors for a successful ISH assay. It was discovered that some procedures enhanced the quality of 2'OMe oligonucleotides probes from the synthesizer: 1) Purification through G50 columns; 2) Measuring spectrally to determine if number of incorporated haptens is consistent with design: and 3) Gel electrophoresis to analyze the size distribution of the probe. Yields from the G50 column purification of 80 nt 2'OMe probes were in the range of 50-90%, with an average of about 65%. Successful probes included at +/−10% of the expected hapten loads, e.g., for an 80 nt 2'OMe probe with 5 DNP, the calculated number based on spectral measurement should be in the range of 4.5-5.5 DNPs per probe molecule.

In some embodiments, the 2'OMe probe has 100% sequence identity to the target RNA sequence. In some embodiments, the 2'OMe probe has between 99%-100% sequence identity to the target RNA sequence. In some embodiments, the 2'OMe probe has between 95%-100% sequence identity to the target RNA sequence. In some embodiments, the 2'OMe probe has between 90%-100% sequence identity to the target RNA sequence. In some embodiments, the 2'OMe probe has between 80%-100% sequence identity to the target RNA sequence. In some embodiments, the 2'OMe probe has between 75%-100% sequence identity to the target RNA sequence.

The present invention also features means of making the target RNA visible. In some embodiments, the means of making the target RNA visible comprises the step of contacting the probes with a detection reagent specific to the probes. Detection reagents are well known in the art. For example, the detection reagent may comprise an antibody or other probe, which binds to the control probe. The detection reagent may comprise a molecule (e.g. enzyme, substrate, tag) that makes the first label of the probe visible. The detection reagent may comprise a plurality of reagents effective for making the probe visible (e.g., more than one antibody, enzyme, substrate, chromogen, etc.). In some embodiments, the detection reagent emits a color. Additional detection reagents (labels, tags, enzymes, substrates, chromogens, antibodies, etc.) are further disclosed herein. The present invention also features means of visualizing the target RNA, wherein the probe (e.g., detectable moiety) is made visible by a detection reagent and the visibility of the detectable moiety is indicative of the target RNA. Means for visualizing labeled probes are well known to one of ordinary skill in the art. For example, in some embodiments, the means for visualizing the target RNA comprises a microscope (e.g., bright field microscope, fluorescence microscope, inverted microscope). In some embodiments, the means for visualizing the target RNA comprises a luminometer. In some embodiments, the means for visualizing the target RNA comprises a radiometric detection machine (e.g., gamma counter, etc.). In some embodiments, the means for visualizing the target RNA comprises a spectrometer. In some embodiments, the means for visualizing the target RNA comprises a real-time PCR machine. In some embodiments, the means for visualizing the target RNA comprises a scintillation and/or luminescence counter. In some embodiments, the means for visualizing the target RNA comprises a colorimeter. Other means for visualizing the target RNA are known in the art.

Without wishing to limit the present invention to any theory or mechanism, it is believed that the probes of the present invention may allow for a reduction in probe concentration required for effective hybridization, e.g., less probe is needed for hybridization and sufficient signal. Thus, the systems of the present invention may help reduce assay costs.

The disclosed methods can be automated. Systems for automated IHC and/or ISH are commercially available, such as the BENCHMARK ULTRA slide staining system, the BENCHMARK XT slide staining system, and the DISCOVERY XT slide staining system (Ventana Medical Systems, Tucson, AZ, BOND-MAX and BOND-III slide stainers (Leica Biosystems, Buffalo Grove, IL), and the IQ Kinetic slide stainer (Biocare Medical, Concord, CA). Ventana Medical Systems, Inc. is the assignee of a number of United States patents disclosing systems and methods for performing automated analyses, including U.S. Pat. Nos. 5,650,327; 5,654,200; 6,296,809; 6,352,861; 6,582,962; 6,827,901 and 6,943,029, each of which is incorporated in its entirety herein by reference.

Non-limiting examples of chromogens that may be used in the disclosed methods include (but are not limited to) those well known to one of ordinary skill in the art, e.g., those described in U.S. Pat. Pub. 2013/0260379 and U.S. Prov. Pat. App. No. 61/831,552, filed Jun. 5, 2013; both of which are incorporated by reference herein in their entirety.

The nucleic acid probes disclosed herein can include one or more labels, for example to permit detection of a target nucleic acid molecule. In various applications, such as in situ hybridization procedures, a nucleic acid probe includes a label (e.g., a detectable label). A "detectable label" is a molecule or material that can be used to produce a detectable signal that indicates the presence or concentration of the probe (particularly the bound or hybridized probe) in a sample. Thus, a labeled nucleic acid molecule provides an indicator of the presence or quantity (for example, gene copy number) of a target nucleic acid (to which the labeled uniquely specific nucleic acid molecule is bound or hybridized) in a sample. The disclosure is not limited to the use of particular labels, although examples are provided.

A label associated with one or more nucleic acid molecules (such as the disclosed probes) can be detected either directly or indirectly. A label can be detected by any known or yet to be discovered mechanism including absorption, emission and/or scattering of a photon (including radio frequency, microwave frequency, infrared frequency, visible frequency and ultra-violet frequency photons), Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected by antibody binding interactions, and paramagnetic and magnetic molecules or materials.

Particular examples of fluorescent molecules (or fluorochromes) are described herein. Numerous fluorochromes are known to those of skill in the art, and can be selected, for example from Life Technologies, e.g., see, The Handbook—A Guide to Fluorescent Probes and Labeling Technologies. Examples of particular fluorophores that can be attached (for example, chemically conjugated) to a nucleic acid molecule (such as a uniquely specific binding region) are provided in U.S. Pat. No. 5,866,366 to Nazarenko et al, (which is incorporated in its entirety by reference herein), such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcoumuarin (Coumarin 151); cyanosine; 4',6-diaminidino-2-phenylindole (DAPI); 5',5''-dibroniopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid: 4,4'-diisothiocyanatostilbene-2,2'-disulfonic acid: 5-[dimethylamino] naphthalene-1-sulfonyl chloride (DNS, dansyl chloride); 4-(4'-dimethylaminophenylazo)benzoic acid (DABCYL): 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRTC); 2',7'-difluorofluorescein (OREGON GREEN®); fluorescamine; IR144; IR1446: Malachite Green isothiocyanate; 4-methylumbelliferone; ortho-cresolphthalein; nitrotyrosine: pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA): tetramethyl rhodamine: tetramethyl rhodamine isothiocyanate (TRITC); riboflavin; rosolic acid and terbium chelate derivatives. Other suitable fluorophores include thiol-reactive europium chelates which emit at approximately 617 nm (Heyduk and Heyduk, Analyt. Biochem. 248:216-27, 1997; J. Biol. Chem. 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et at, which is incorporated in its entirety by reference herein) and derivatives thereof. Other fluorophores known to those skilled in the art can also be used, for example those available from Life Technologies (Carlsbad, CA) and including the ALEXA FLUOR® series of dyes (for example, as described in U.S. Pat. Nos. 5,696, 157, 6,130,101 and 6,716,979), the BODIPY series of dyes (dipyrrometheneboron difluoride dyes, for example as described in U.S. Pat. Nos. 4,774,339, 5,187,288, 5,248,782, 5,274,113, 3,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912), the disclosures of which are incorporated in their entirety herein by reference. In addition to the fluorochromes described above, a fluorescent label can be a fluorescent nanoparticle, such as a semiconductor nanocrystal, e.g., a quantum dot (obtained, for example, from Life Technologies): see also, U.S. Pat. Nos. 6,815,064; 6,682, 596; and 6,649,138, the disclosures of which are incorporated in their entirety herein by reference). Semiconductor nanocrystals are microscopic particles having size-dependent optical and/or electrical properties. When semiconductor nanocrystals are illuminated with a primary energy source, a secondary emission of energy occurs of a frequency that corresponds to the handgap of the semiconductor material used in the semiconductor nanocrystal. This emission can be detected as colored light of a specific wavelength or fluorescence. Semiconductor nanocrystals with different spectral characteristics are described in e.g., U.S. Pat. No. 6,602,671. Semiconductor nanocrystal that can be coupled to a variety of biological molecules (including dNTPs and/or nucleic acids) or substrates by techniques described in, for example, Bruchez et al., Science 281:2013-2016, 1998; Chan et al., Science 281:2016-2018, 1998: and U.S. Pat. No. 6,274,323, the disclosures of which are incorporated in their entirety herein by reference. Formation of semiconductor nanocrystals of various compositions are disclosed in, e.g., U.S. Pat. Nos. 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Publication No. 2003/0165951 as well as PCT Publication No. WO 99/26299, the disclosures of which are incorporated in their entirety herein by reference. Separate populations of semiconductor nanocrystals can be produced that are identifiable based on their different spectral characteristics. For example, semiconductor nanocrystals can be produced that emit light of different colors based on their composition, size or size and composition. For example, quantum dots that emit light at different wavelengths based on size (565 nm, 655 nm, 705 nm, or 800 nm emission wavelengths), which are suitable as fluorescent labels in the probes disclosed herein are available from Life Technologies (Carlsbad, CA).

Additional labels include, for example, radioisotopes (such as 3H), metal chelates such as DOTA and DPTA chelates of radioactive or paramagnetic metal ions like Gd3+, and liposomes.

Detectable labels that can be used with nucleic acid molecules (such as the disclosed probes) also include enzymes, for example horseradish peroxidase (HRP), alkaline phosphatase (AP), acid phosphatase, glucose oxidase, β-galactosidase, β-glucuronidase, or P-lactamase. Where the detectable label includes an enzyme, a chromogen, fluorogenic compound, or luminogenic compound can be used in combination with the enzyme to generate a detectable signal (numerous of such compounds are commercially available, for example, from Life Technologies). Particular examples of chromogenic compounds include diaminobenzidine (DAB), 4-nitrophenylphosphate (pNPP), fast red, fast blue, bromochloroindolyl phosphate (BCIP), nitro blue tetrazolium (NBT), BCIP/NBT. AP Orange, AP blue, tetramethylbenzidine (TMB), 2,2'-azino-di-[3-ethylbenzthiazoline sulphonate] (ABTS), o-dianisidine, 4-chloronaphthol (4-CN), nitrophenyl-β-D-galactopyranoide (ONPG), o-phenylenediamine (OPD), 5-bromo-4-chloro-3-indolyl-β-galatopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrocetrazolium (INT), tetrazolium blue, and tetrazolium violet.

Alternatively, an enzyme can be used in a metallographic detection scheme. For example, silver in situ hybridization (SISH) procedures involve metallographic detection schemes for identification and localization of a hybridized genomic target nucleic acid sequence. Metallographic detection methods include using an enzyme, such as alkaline phosphatase, in combination with a water-soluble metal ion and a redox-inactive substrate of the enzyme. The substrate is converted to a redox-active agent by the enzyme, and the redox-active agent reduces the metal ion, causing it to form a detectable precipitate. (See, for example, U.S. Patent Application Publication No. 2005/0100976, PCT Publication No. 2005/003777 and U.S. Patent Application Publication No. 2004/0265922 the disclosures of which are incorporated in their entirety herein by reference). Metallographic detection methods also include using an oxido-reductase enzyme (such as horseradish peroxidase) along with a water soluble metal ion, an oxidizing agent and a reducing agent, again to form a detectable precipitate. (See, for example, U.S. Pat. No. 6,670,113).

In non-limiting examples, the disclosed nucleic acid probes are labeled with hapten molecules (such as a nitroaromatic compound (e.g., 2,4-dinitrophenyl (DNP)), biotin, fluorescein, digoxigenin, etc.). Additional haptens suitable for labeling the disclosed probes include nitropyrazole, 3-hydroxyquinoxaline, thiazolesulfonamide, nitrocinnamic acid, rotenone, 7-(diethylamino)coumarin-3-carboxylic acid, benzodiazepine, or benzofuran haptens (see, e.g., International Pat. Publ. No. WO 2012/003476, incorporated herein by reference). Methods for conjugating haptens and other labels to dNTPs (e.g., to facilitate incorporation into labeled probes) are well known in the art. For examples of procedures, see, e.g., U.S. Pat. Nos. 5,258,507, 4,772,691, 5,328,824, and 4,711,955, the disclosures of which are incorporated in their entirety herein by reference. Indeed, numerous labeled dNTPs are available commercially, for example from Life Technologies (Carlsbad, CA). A label can be directly or indirectly attached to a dNTP at any location on the dNTP, such as a phosphate (e.g., α, β or γ phosphate) or a sugar.

Detection of labeled nucleic acid molecules can be accomplished by contacting the hapten-labeled nucleic acid molecules bound to the genomic target nucleic acid with a primary anti-hapten antibody. In one example, the primary anti-hapten antibody (such as a mouse anti-hapten antibody) is directly labeled with an enzyme. In another example, a secondary anti-antibody conjugated to an enzyme is used for signal amplification. In CISH a chromogenic substrate is added, for SISH, silver ions and other reagents as outlined in the referenced patents/applications are added.

In some examples, a probe is labeled by incorporating one or more labeled dNTPs using an enzymatic (polymerization) reaction. For example, the disclosed nucleic acid probes (for example, incorporated into a plasmid vector) can be labeled by nick translation (using, for example, biotin, DNP, digoxigenin, etc.) or by random primer extension with terminal transferase (e.g., 3' end tailing). In some examples, the nucleic probe is labeled by a modified nick translation reaction where the ratio of DNA polymerase I to deoxyribonuclease I (DNase 1) is modified to produce greater than 100% of the starting material. In particular examples, the nick translation reaction includes DNA polymerse I to DNase 1 at a ratio of at least about 800:1, such as at least 2000:1, at least 4000:1, at least 8000:1, at least 10.000:1, at least 12,000:1, at least 16,000:1, such as about 800:1 to 24,000:1 and the reaction is carried out overnight (for example, for about 16-22 hours) at a substantially isothermal temperature, for example, at about 16° C. to 25° C. (such as room temperature). If the probe is included in a probe set (for example, multiple plasmids, such as 2, 3, 4, 5, 6, 7, 8, 9, 10, or more plasmids), the plasmids may be mixed in an equal molar ratio prior to performing the labeling reaction (such as nick translation or modified nick translation).

In other examples, chemical labeling procedures can also be employed. Numerous reagents (including hapten, fluorophore, and other labeled nucleotides) and other kits are commercially available for enzymatic labeling of nucleic acids, including the disclosed nucleic acid probes. As will be apparent to those of skill in the art, any of the labels and detection procedures disclosed above are applicable in the context of labeling a probe, e.g., for use in in situ hybridization reactions. For example, the Amersham MULTIPRIME® DNA labeling system, various specific reagents and kits available from Molecular Probes/Life Technologies, or any other similar reagents or kits can be used to label the nucleic acids disclosed herein. In particular examples, the disclosed probes can be directly or indirectly labeled with a hapten, a ligand, a fluorescent moiety (e.g., a fluorophore or a semiconductor nanocrystal), a chromogenic moiety, or a radioisotope. For example, for indirect labeling, the label can be attached to nucleic acid molecules via a linker (e.g., PEG or biotin). Additional methods that can be used to label probe nucleic acid molecules are provided in U.S. Application Pub. No. 2005/0158770, the disclosure of which is incorporated in its entirety herein by reference.

Further examples of haptens are described in U.S. Pat. No. 8,846,320 and related patents (e.g., U.S. Pat. No. 7,695,929; U.S. Provisional Application No. 60/856,133), the disclosures of which are incorporated in their entirety herein by reference.

Without wishing to limit the present invention to any theory or mechanism, it is believed that the performance of the tyramide-hapten conjugates may be related to the haptens themselves. For example, the haptens may influence (e.g., in unexpected ways) the generation of reactive tyramide-intermediates and/or overall performance of the reagents.

Without wishing to limit the present invention to any theory or mechanism, it is believed that it cannot necessarily be predicted which hapten will work best with the tyramide amplification system.

Since microRNAs are so short, it is expected that microRNA detection would require the use of a single probe. It was surprisingly discovered that the tyramide-hapten amplification system and '2-O-methyl RNA oligonucleotide probes were robust enough to detect microRNA targets.

III. Detailed RNA In Situ Hybridizations and Tyramide-Chromogen Detection

Formalin-fixed, paraffin-embedded tissues (FFPET) mounted on SUPERFROST slides were de-paraffined and antigen retrieved using CC1 reagent and protease 3 (Ventana Medical Systems, Inc. Catalog #: 760-2020). Following retrieval, one drop (100 μL) of hapten-labeled 2'O-methyl modified synthetic experimental antisense or control scrambled probes were dispensed onto a slide, denatured at 80° C. for 8 min, and hybridized at 75° C. for 2 hrs for 80 nucleotide probes against target RNA or 45° C. for 2 hrs for 25 nucleotide probes against miRNA (microRNA). Following hybridization, slides were washed 3 times using EZ Prep (Ventana Medical Systems. Inc. Catalog #: 950-102) at 75° C. for 8 min. for RNA 80 nucleotide probes or 4 washes using 2×SSC at 45° C. for 4 min for 25 nucleotide probes against miRNA to remove non-specifically hybridized probe.

Figure 2:
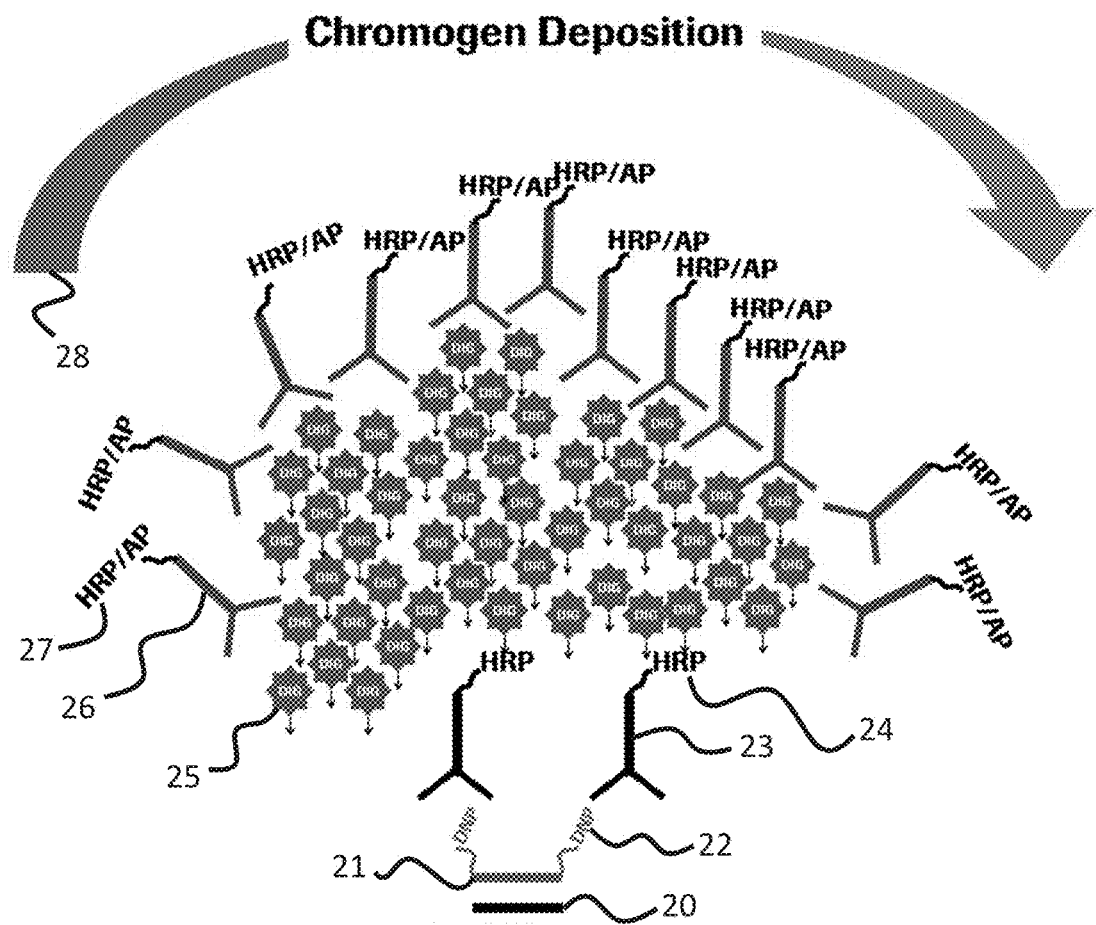
FIG. 2 shows a schematic representation of a method for detecting probes of the present invention.

It was discovered that a series of amplifications were advantageous for detecting the miRNA in a bright-field microscope (e.g., chromogenically). For the detection, tyramide-chromogen conjugates were used. Reference is made to U.S. Patent Publication No. 2013/0260379, which is hereby incorporated by reference herein for disclosure related to detection chemistries. Use of a one-tiered amplification strategy, involving an anti-hapten-HRP conjugate to catalyze deposition of tyramide-chromogen conjugate, did not generate a discernable signal. Referring now to FIG. 2, shown is a schematic drawing representing the detection approach. In particular, a target 20 is detected by a probe 21 labeled with a hapten 22. An anti-hapten antibody 23 conjugated to an enzyme 24 then is contacted to the sample so that antibody 23 binds to probe 21 and links enzyme 24 to target 20. Enzyme 24 catalyzes deposition of a tyramide-hapten conjugate 25. A plurality of tyramide-hapten conjugate 25 binds to the sample in the vicinity of target 20, thus substantially amplifying the signal associated with target 20. A second enzyme-conjugated anti-hapten antibody 26 is then contacted to the sample and allowed to bind to tyramide-hapten conjugate 25. The second enzyme 27 can then be used to catalyze deposition of a tyramide-chromogen conjugate, silver deposition (Ventana Medical Systems, Inc. Catalog #:780-001), or any other chromogen desired. The final chromogen deposition is depicted as arrow 28 since the level of amplification compared to signal 20 would be very substantial.

Figure 3:
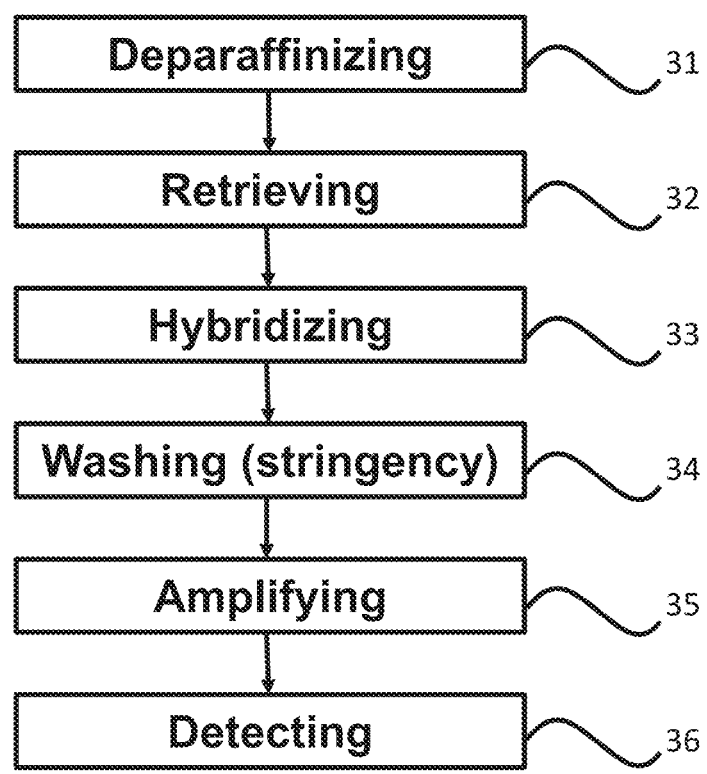
FIG. 3 shows a flow chart showing exemplary steps for using 2'-O-methyl RNA probes in an assay.

Referring now to FIG. 3, shown is a flow chart showing exemplary steps for using 2-O-methyl RNA probes in an assay. Deparaffinizing the FFPET sample 31 is followed by retrieving the RNA for detection 32 (e.g. mild CC1 or CC2), hybridizing 33 the probes to the target, washing 34 to stringency, amplifying 35 signal, and detecting 36 with a chromogen.

Amplification and detection of each haptenated probe was accomplished as follows. Endogenous tissue peroxidase activity was inactivated by dispensing three times of one drop PO inhibitor (Ventana Medical Systems, Inc. Catalog #: 760-4143) and incubating the reaction for 12 min. Following several washes one drop of TSA block (Ventana Medical Systems, Inc. Catalog #: 760-4142) was dispensed onto the slide and incubated 4 min, before a dispensing a drop of RP-conjugated anti-hapten monoclonal antibody (2.5 ug/ml prepared in avivdin diluent plus B5 blocker, part no. 90040); the mixture was incubated for 28 min.

Tyramide-mediated hapten amplification was accomplished by dispensing one drop of tyramide-hapten conjugate on the slide followed by one drop TSA-$H_2O_2$ (Ventana Medical Systems, Inc. Catalog #: 760-4141) and incubating the reaction for 32 min. Following extensive washing another drop of TSA block was dispensed followed by a drop of cognate anti-hapten HRP conjugated antibody incubated for 28 minutes. Following washing this HRP conjugate catalyzed silver chromogen deposition as directed by the manufacturer (Ventana Medical Systems, Inc. Catalog #: 780-001). Tissue nuclei were then stained using Hematoxylin II and bluing reagent; slides were then dehydrated using gradient alcohols and coverslipped.

IV. Methods and Results

The automated technology described has a modularized design, which is briefly described below.

1) Formalin fixed paraffin-embedded tissue (FFPET) samples on glass slides are treated to remove the wax, to denature cross-linked proteins, and with a limited amount of protease to permit probe and detection reagent permeability.

2) Hapten-labelled probe(s) are hybridized to targets in a hybridization buffer, followed by stringent washes to remove free probes.

3) HRP conjugated anti-hapten mouse monoclonal antibody is incubated with hybridized probes, followed by extensive washes to remove antibodies not bound to haptens on probes.

4) A tyramide amplification step is carried out with hapten labelled tyramide compound and free tyramide is washed away.

5) A second HRP conjugated anti-hapten mouse monoclonal antibody is incubated with haptens deposited by the tyramide reaction and excess antibodies not bound are washed away.

6) In situ bound HRP catalyzes silver or alternative chromogenic deposition, and signals are visualized under a microscope on slides for detection and semi-quantification of RNA expression.

Example 1

MicroRNA ISH Staining Consistent with Array Quantification

To establish that the probes could be used to semi-quantitatively detect miRNA in tissues having known concentrations. MCF-7 xenografts were analyzed, miRNA probes were selected based on the report by Fix et al. *Cancer Genomics & Proteomics* 7:261-278. The authors used a microRNA microarray to profile and quantify 871 human miRNAs from MCF-7 cultured cells treated with or without polyphenon-60. The MCF-7 tissue was assayed for miR-200c, which was reported as having between 10000-20000 copies per sample, miR-21, which was reported as having >20000 copies per sample, miR-25, which was reported as having between 5000-1000 copies per sample.

Figure 4A:
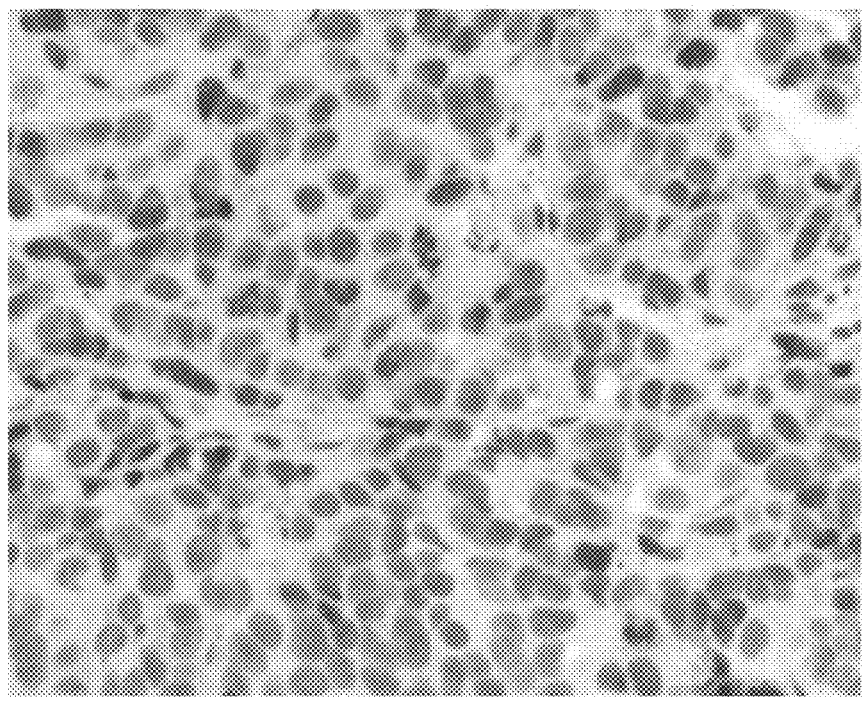
FIG. 4A is a MCF-7 xenograft tissue sample stained using a scramble probe as a control to establish the background staining.
Figure 4B:
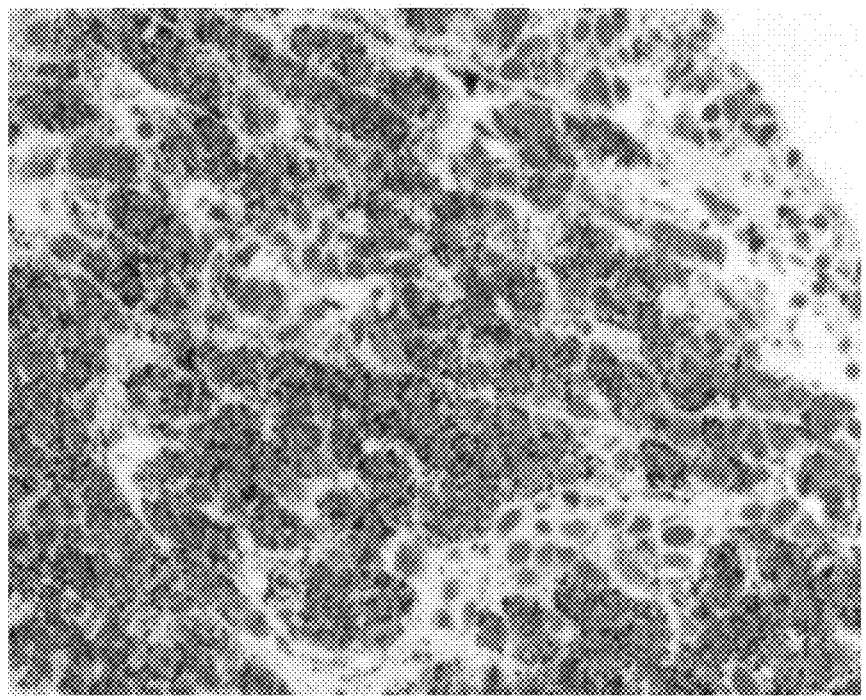
FIG. 4B shows staining of MCF-7 xenograft tissue with the miR-200c probe.
Figure 4C:
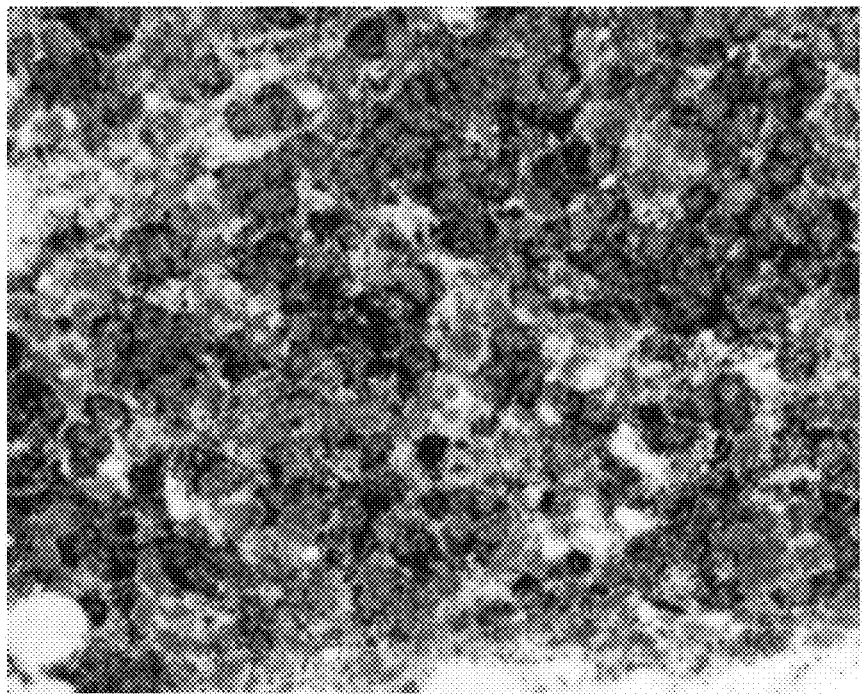
FIG. 4C shows the staining of MCF-7 xenograft tissue with the miR-21 probe.
Figure 4D:
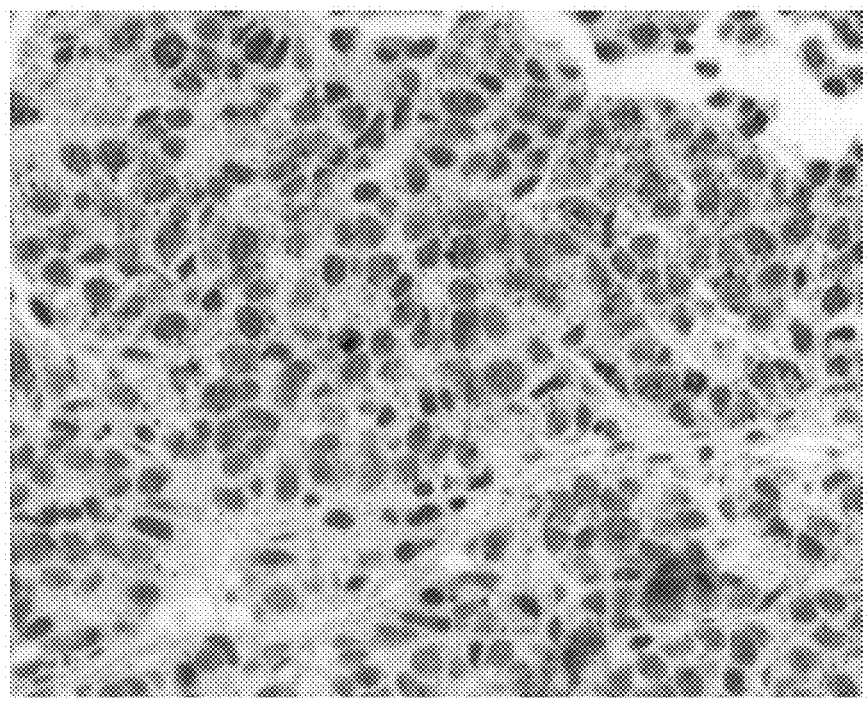
FIG. 4D shows the staining of MCF-7 xenograft tissue with the miR-25 probe.

DNP-labeled (5' and 3 ends) 22 base 2'-O-methyl RNA oligonucleotide probes, directed against four microRNA targets expressed at various levels in MCF-7 cells, were synthesized and combined with a modified VENTANA OptiView amplification detection kit and silver detection; the fully automated staining assay was accomplished using a VENTANA Benchmark XT® instrument. The probes and new detection system catalyzed sensitive and specific detection of each microRNA target in MCF-7 xenograft FFPE tissue. The results are shown in FIG. 4, wherein FIG. 4A is a sample stained using a scramble probe as a control to establish the background staining. FIG. 4B shows the staining with the miR-200c probe FIG. 4C shows the staining with the miR-21 probe; and FIG. 4D shows the staining with the miR-25 probe. Consistent with the published results, the miR-21 exhibited the darkest staining, followed by the miR-200c, and then the miR-25. The scrambled probe did not generate substantial background. The results indicate that miRNA can be semiquantitatively detected in FFPET using the probes and methods described herein. Of note is that the detection can be further amplified or amplified less than shown so as to modify the sensitivity of the staining.

A gradient of cytoplasmic microRNA signals was observed in normal fixed xenograft tissue (strong signal on tissue periphery; weaker signal as move to tissue center) suggesting a fixation influence on microRNA detection. A more uniform signal pattern was observed using "2+2" fixed MCF-7 xenograft tissue suggesting that utility of this new fixation method might be extended to include microRNA targets.

Figure 5A:
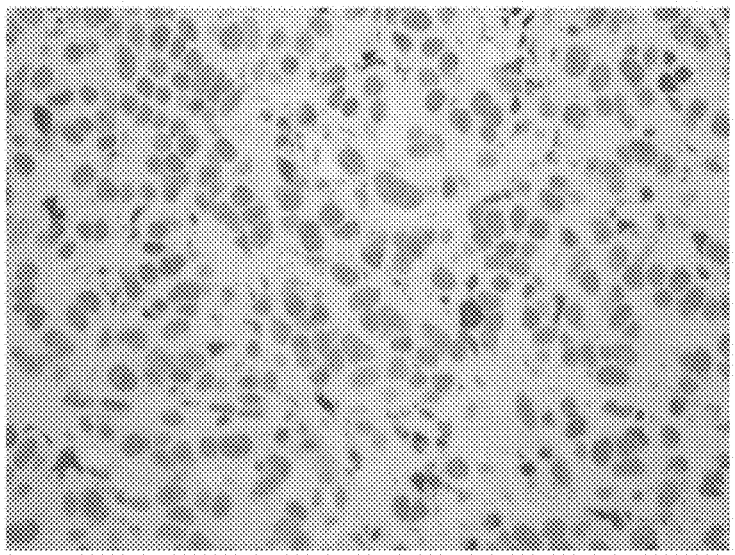
FIG. 5A shows miRNA staining of MCF-7 xenograft tissue after fixation with room temperature 10% NBF for 24 hours using negative control scrambled probes.
Figure 5B:
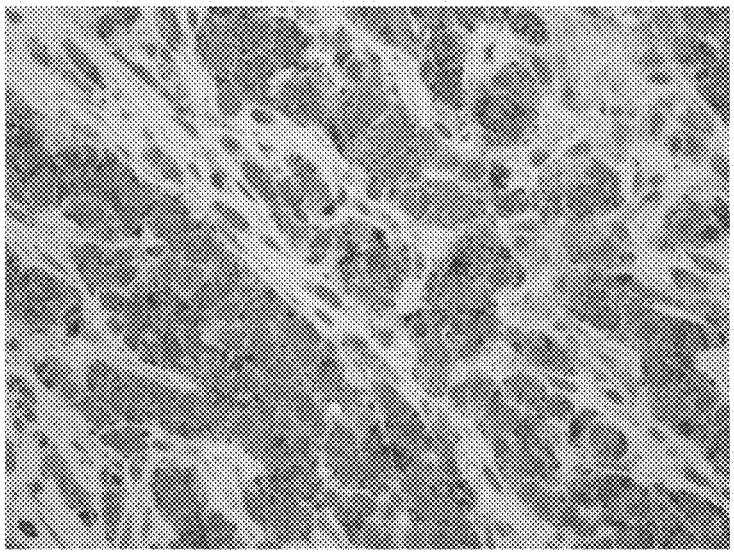
FIG. 5B shows miRNA staining of MCF-7 xenograft tissue after fixation with room temperature 10% NBF for 24 hours using miR-21 probes.
Figure 5C:
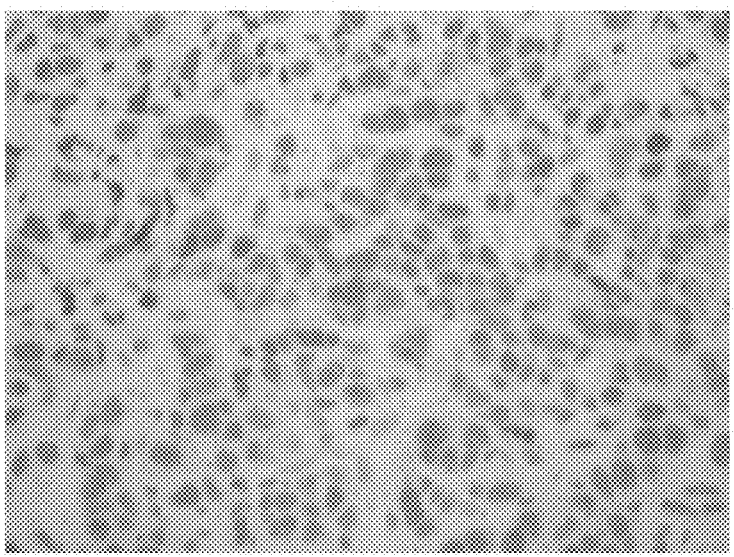
FIG. 5C shows miRNA staining of MCF-7 xenograft tissue after fixation with room temperature 10% NBF for 24 hours using miR-200c probes.

To test the impact of fixation on staining, MCF-7 xenograft tissues were harvested and immediately put in room temperature or cold 10% NBF under various conditions. FIGS. 5-9 show photomicrographs of miRNA staining of (A) negative control scrambled probes, (B) miR-21 probes, and (C) miR-200c probes. FIG. 5 shows fixation using room temperature 10% NBF (neutral buffered formalin) for 24 hours. The 24-hour room temperature slide is the desired standard to which processing protocols are compared as disclosed in the '195 application. See FIG. 5 of the '195 application. For purposes of this section dealing with the impact of fixation on tissue staining, a general discussion is supplied herein which is disclosed in the '195 application.

As disclosed in the '195 patent application, the first step of the process is to subject a tissue sample to fixative composition under conditions effective to allow substantially complete diffusion of the composition throughout substantially the entire cross section of the sample. An effective temperature range for the first step is from greater than −20 degrees Celsius to at least 15 degrees Celsius, preferably greater than 0 degrees Celsius to an upper temperature more typically about 10 degrees Celsius, and even more typically from about 3 degrees Celsius to about 5 degrees Celsius. For working embodiments, the temperature typically was about 4 degrees Celsius.

According to the teachings of the '195 patent application, as the temperature increases, the rate of cross-linking increases. And this first processing step attempts to balance the beneficial properties associated with substantially complete diffusion of fixative composition throughout the entire cross section of the tissue sample while minimizing the effects associated with initializing cross-linking. However, diffusion also increases with increasing temperature, and so for a given sample, it was found that maximizing the rate of diffusion while minimizing any deleterious effects associated with increased cross-linking rate appeared to increase benefits.

The teaching continues that diffusion of the fixative composition into the tissue sample is generally continued for a time period effective for diffusion of the composition throughout substantially the entire cross section of the sample. The time period for the first processing step ranges from about 15 minutes up to about 4 hours, most typically from greater than 15 minutes to about 3 hours, with good results typically being obtained by conducting the fixative composition diffusion step for about 1.5 hours to about 2 hours.

The '195 patent application also teaches that the temperature associated with the second processing step typically is higher than ambient, such as higher than about 22 degrees Celsius. For working embodiments set forth in the application, the temperature typically was greater than ambient up to at least 55 degrees Celsius, more typically from about 35 degrees Celsius to about 45 degrees Celsius, as this temperature range increased the cross-linking kinetics sufficiently to allow relatively quick tissue cross-linking. The time period for the second processing step ranges from greater than 15 minutes up to at least about 5 hours, more typically is at least about 1 hour to about 4 hours, and more typically is from about 2 hours to about 3 hours. Certain disclosed working embodiments in the '195 application were practiced where the second processing step was for 1.5 hours at 45 degrees Celsius.

Referring to the '195 patent application as an example, therein FIGS. 4A and 4B are enhanced images of FIGS. 3G and 3H of the same application. The arrows therein relative to FIG. 4B illustrate the enhanced detail that results for images produced using a 2 hour pre-soak in 10% formalin fixation solution at 4 degrees Celsius for these exemplary embodiments. The tissue morphology is shown to be better for the tissue samples produced using a 2 hour pre-soak in 10% formalin fixation solution at 4 degrees Celsius. For tissue samples that were not subjected to a 2 hour pre-soak in 10% formalin fixation solution at 4 degrees Celsius, formalin did not diffuse into the interior—see the morphology of the sample (FIG. 4A) which is not as preserved as was the morphology of the tissue sample (FIG. 4B) produced using a 2 hour pre-soak in 10% formalin fixation solution at 4 degrees Celsius. The foregoing is a brief description and teachings of the 2+2 methodology as detailed in the '195 patent application and applied herein.

Figure 6A:
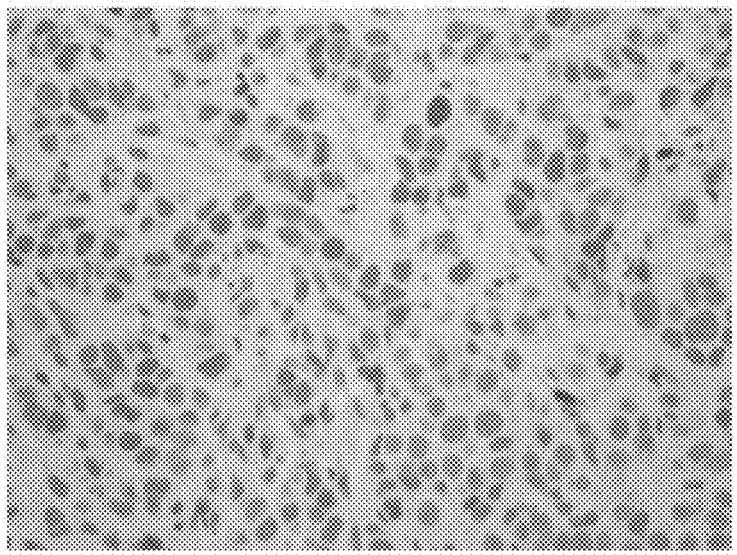
FIG. 6A shows miRNA staining of MCF-7 xenograft tissue after fixation for 2 hours with 4° C. NBF followed by 2 hours of 45° C. NBF using negative control scrambled probes.
Figure 6B:
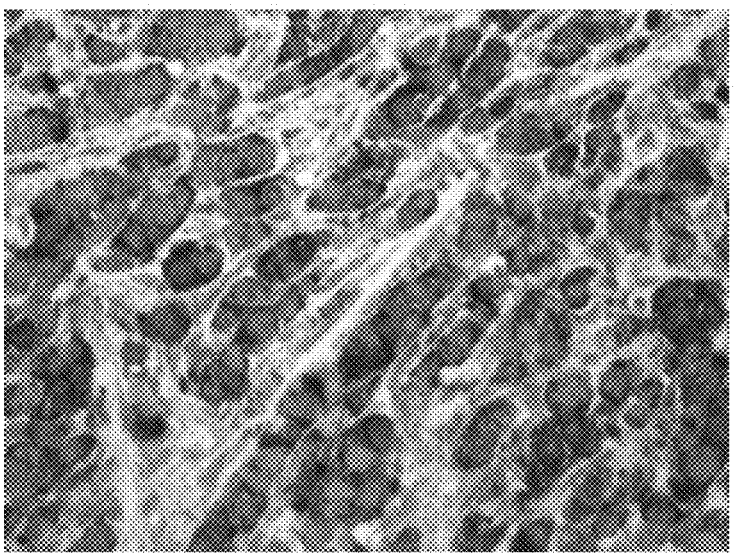
FIG. 6B shows miRNA staining of MCF-7 xenograft tissue after fixation for 2 hours with 4° C. NBF followed by 2 hours of 45° C. NBF using miR-21 probes.
Figure 6C:
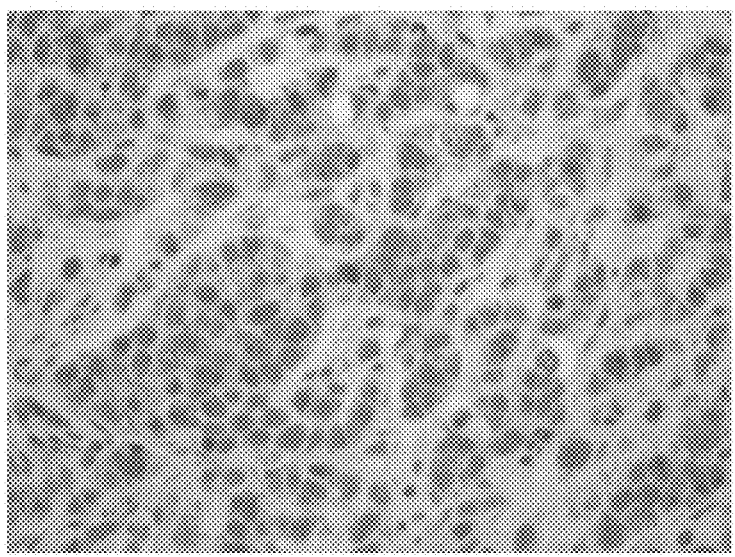
FIG. 6C shows miRNA staining of MCF-7 xenograft tissue after fixation for 2 hours with 4° C. NBF followed by 2 hours of 45° C. NBF using miR-200c probes.
Figure 7A:
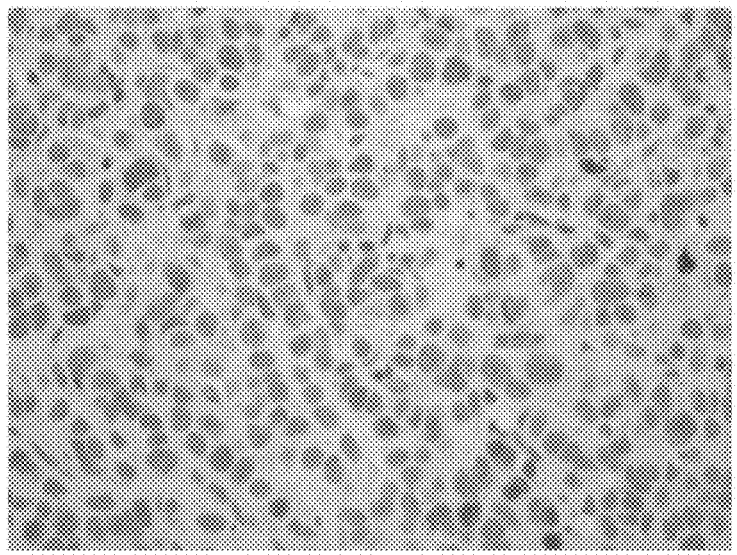
FIG. 7A shows miRNA staining of MCF-7 xenograft tissue after fixation for 4 hours with 4° C. NBF followed by 2 hours of 45° C. NBF using negative control scrambled probes.
Figure 7B:
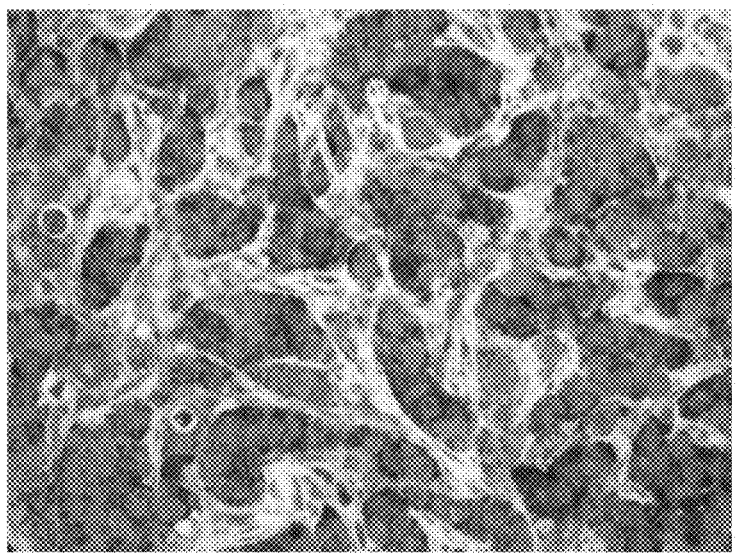
FIG. 7B shows miRNA staining of MCF-7 xenograft tissue after fixation for 4 hours with 4° C. NBF followed by 2 hours of 45° C. NBF using miR-21 probes.
Figure 7C:
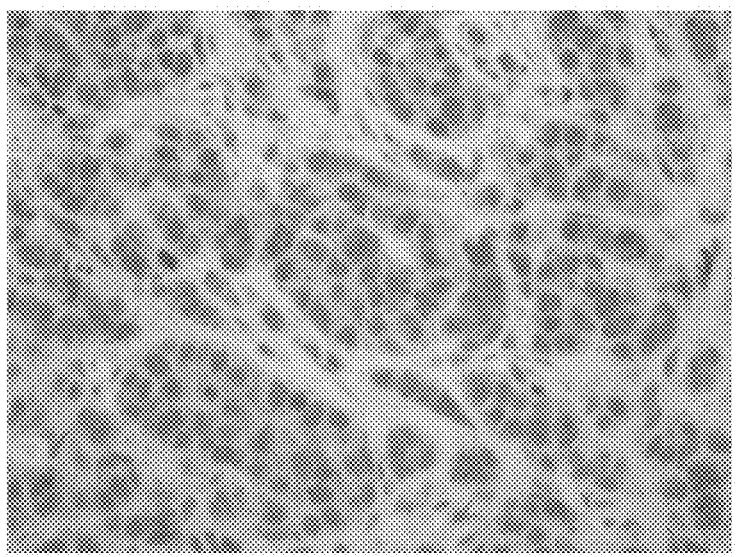
FIG. 7C shows miRNA staining of MCF-7 xenograft tissue after fixation for 4 hours with 4° C. NBF followed by 2 hours of 45° C. NBF using miR-200c probes.
Figure 8A:
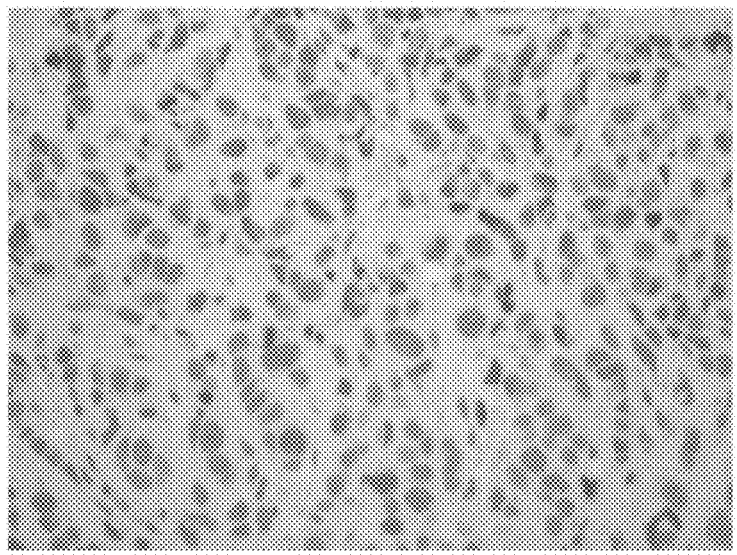
FIG. 8A shows miRNA staining of MCF-7 xenograft tissue after fixation for 6 hours with 4° C. NBF followed by 2 hours of 45° C. NBF using negative control scrambled probes.
Figure 8B:
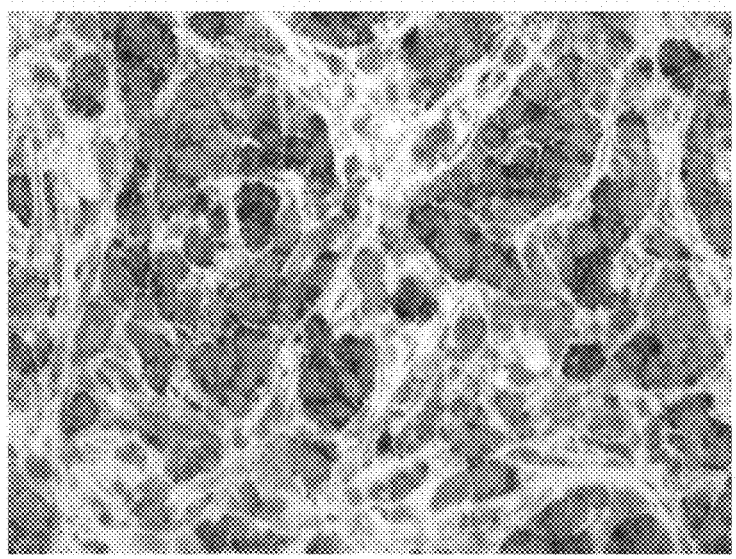
FIG. 8B shows miRNA staining of MCF-7 xenograft tissue after fixation for 6 hours with 4° C. NBF followed by 2 hours of 45° C. NBF using miR-21 probes.
Figure 8C:
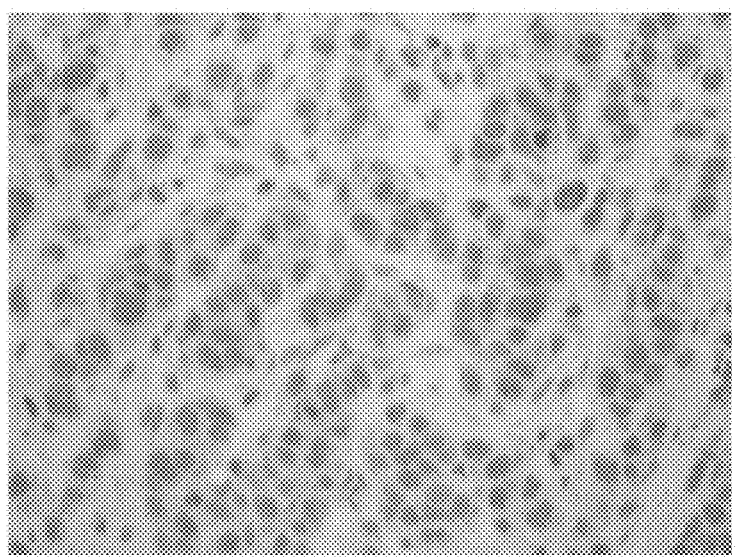
FIG. 8C shows miRNA staining of MCF-7 xenograft tissue after fixation for 6 hours with 4° C. NBF followed by 2 hours of 45° C. NBF using miR-200c probes.
Figure 9A:
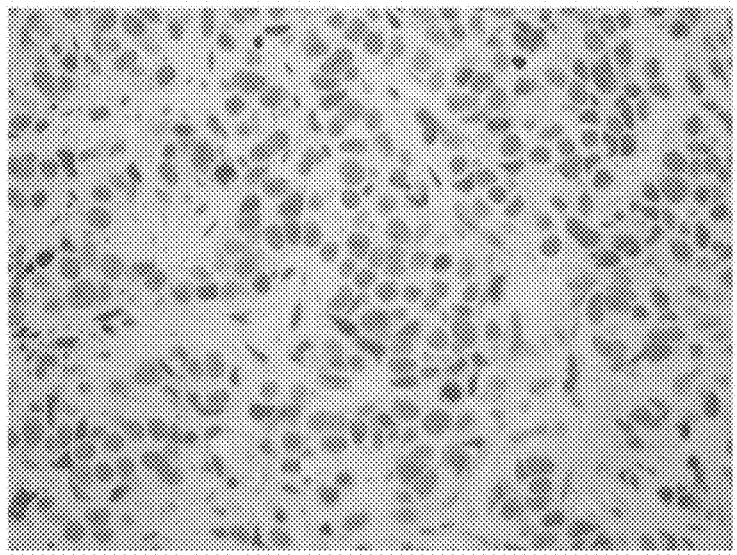
FIG. 9A shows miRNA staining of MCF-7 xenograft tissue after fixation for 24 hours with 4° C. NBF followed by 2 hours of 45° C. NBF using negative control scrambled probes.
Figure 9B:
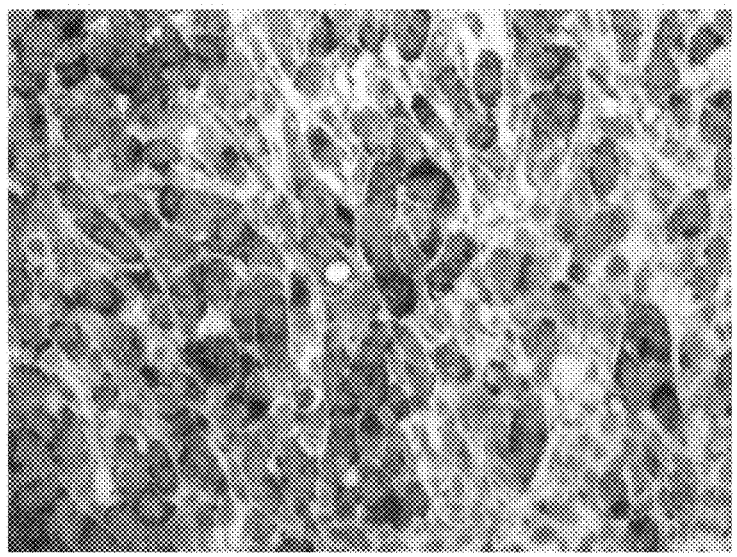
FIG. 9B shows miRNA staining of MCF-7 xenograft tissue after fixation for 24 hours with 4° C. NBF followed by 2 hours of 45° C. NBF using miR-21 probes.
Figure 9C:
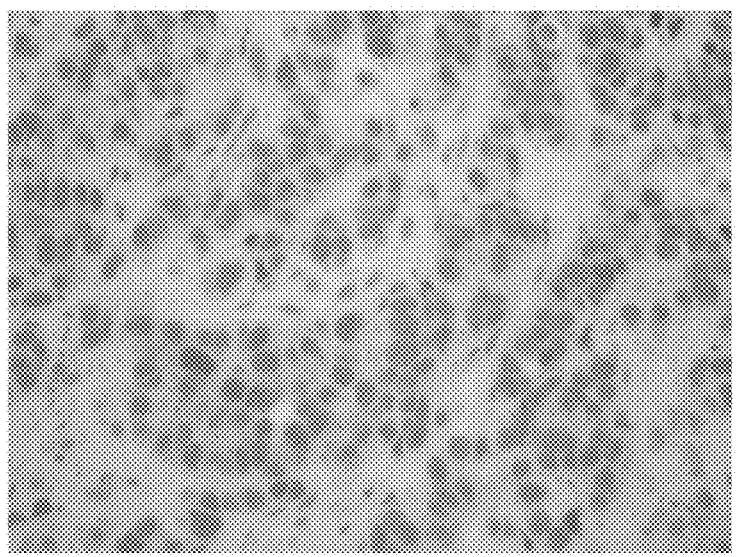
FIG. 9C shows miRNA staining of MCF-7 xenograft tissue after fixation for 24 hours with 4° C. NBF followed by 2 hours of 45° C. NBF using miR-200c probes.

FIG. 6 shows fixation using 2 hours of 4° C. NBF followed by 2 hours of 45° C. NBF; FIG. 7 shows fixation using 4 hours of 4° C. NBF followed by 2 hours of 45° C. NBF; FIG. 8 shows fixation using 6 hours of 4° C. NBF followed by 2 hours of 45° C. NBF; FIG. 9 shows fixation using 24 hours of 4° C. NBF followed by 2 hours of 45° C. NBF. From FIGS. 5-9, it appears that the best signal to noise ratio for these particular microRNAs can be seen for those samples treated with either the "2+2" (FIG. 6) or "4+2" (FIG. 7) fixation method.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other reference mentioned herein are expressly incorporated by reference in their entirety, to the same extent as if each were incorporated by reference individually. In case of conflict, the present specification, including definitions, will control.

Other aspects are set forth within the following claims.

The invention claimed is:

1. A system for bright field in situ hybridization comprising:
   a probe set comprising at least two first target probes, wherein each of the at least two first target probes are specific to different portions of a first target RNA, wherein each of the at least two first target probes are conjugated to least one detectable moiety, and wherein the at least two first target probes consist of 2'-O-methyl nucleotides; and
   a reactive chromogen conjugate system effective for signal amplification, wherein each reactive chromogen conjugate system is adapted to bind to the at least one detectable moiety of each first target probe of the at least two first target probes.

2. The system of claim 1, wherein the at least two first target probes each comprise between 15 to 30 nucleotides, between 20 to 50 nucleotides, between 40 to 80 nucleotides, between 20 to 100 nucleotides, or between 20 to 200 nucleotides in length.

3. The system of claim 1, wherein the at least two first target probes are each conjugated with at least two detectable moieties, at least three detectable moieties, at least four detectable moieties, or at least five detectable moieties.

4. The system of claim 1, wherein the detectable moiety comprises a hapten.

5. The system of claim 4, wherein the hapten is selected from the group consisting of dinitrophenol (DNP), nitropyrazole, hydroxyquinoxaline, thiazolesulfonamide, nitrocinnamic acid, rotenone, 7-(diethylamino) coumarin-3-carboxylic acid, benzodiazepine, and benzofuran.

6. The system of claim 1, wherein the reactive chromogen conjugate system comprises a tyramide-hapten conjugate.

7. The system of claim 1, wherein the at least two first target probes each comprise at least one detectable moiety per 20 base pairs of the target probe.

8. The system of claim 1, further comprising a means of making a target microRNA visible.

9. The system of claim 8, wherein the means of making the target microRNA visible comprises means for contacting the probes with the reactive chromogen conjugate system specific to the detectable moieties of the probes, wherein the reactive chromogen conjugate system emits a color.

10. The system of claim 8, further comprising a means of visualizing the target microRNA, wherein the detectable moieties are made visible by the reactive chromogen conjugate system, the visibility of the detectable moieties being indicative of the target microRNA.

11. The system of claim 10, wherein the means of visualizing the target microRNA comprises a bright field microscope.

12. A method of bright field in situ hybridization comprising:
   contacting a sample with an antigen retrieval reagent;
   contacting the sample with a probe of the system according to any of claims 1-3 and 4-11 under conditions sufficient that the target probe hybridizes to the target RNA in the sample;
   rinsing the sample to remove unbound probe; and
   detecting the target RNA by making visible the detectable moiety.

13. The method of claim 12, wherein the method uses conditions that preserve cell morphology.

14. A method of in situ hybridization comprising:
   contacting a sample with a probe set specific for a target RNA under conditions sufficient that the probe set hybridizes to the target RNA in the sample, wherein the probe set comprises at least two first target probes, wherein each of the at least two first target probes are specific to different portions of a first target RNA, wherein each of the at least two first target probes are conjugated to least one detectable moiety, and wherein the at least two first target probes consist of 2'-O-methyl nucleotides;

contacting the sample with a first anti-detectable moiety antibody conjugated with a first enzyme, the first anti-detectable moiety antibody being specific for the at least two target probes;

contacting the sample with a reactive chromogen conjugate, wherein the first enzyme of the first anti-detectable moiety antibody binds the reactive chromogen conjugate to the first anti-detectable moiety antibody and/or surrounding tissue; and contacting the sample with a second antibody conjugated with a second enzyme, the second antibody is specific for the reactive chromogen conjugate, wherein the second enzyme catalyzes visibility of the chromogen, and wherein visibility of the chromogen is indicative of the target RNA.

15. A method of in situ hybridization comprising:

contacting a sample with at least two first target probes, where each of the at least two first target probes consist of 2'-O-methyl nucleotides and wherein each of the at least two first target probes are specific to different portions of a first target RNA in the sample; wherein the sample is contacted with the at least two first target probes under conditions sufficient that the at least two first target probes hybridizes to the first target RNA in the sample, wherein the at least two first target probes are each conjugated with at least one detectable moiety disposed at either the 5' end or the 3' end of the at least two first target probes, and wherein each of the at least two first target probes are between 15 to 30 nucleotides in length;

contacting the sample with a first anti-detectable moiety antibody conjugated with a first enzyme, wherein the first anti-detectable moiety antibody is specific for the at least one detectable moiety disposed at either the 5' end or the 3' end of the at least two first target probes;

contacting the sample with reactive chromogen conjugate, wherein the first enzyme of the first anti-detectable moiety antibody binds the reactive chromogen conjugate to the first anti-detectable moiety antibody; and contacting the sample with a second antibody conjugated with a second enzyme, wherein the second antibody is specific for the reactive chromogen conjugate, wherein the second enzyme catalyzes visibility of the chromogen, wherein visibility of the chromogen is indicative of the target RNA.

16. The method of claim 15, wherein each of the at least two target probes are conjugated with to two detectable moieties.

17. The method of claim 15, wherein the detectable moiety comprises dinitrophenol (DNP).

18. The method of claim 16, wherein a first hapten is located at a 3' end of the probe, and a second hapten is located at a 5' end of the probe.

19. The method of claim 15, wherein the reactive chromogen conjugate comprises a tyramide chromogen conjugate.

20. The system of claim 1, further comprising at least one second target probe, wherein the at least one second target probe is specific to at least a portion of a second target RNA, wherein the at least one second target probe consists of 2'O-methyl RNA oligonucleotides; and wherein the system further comprises a second reactive chromogen conjugate system.

21. The system of claim 20, wherein the second reactive chromogen conjugate system comprises a second tyramide-happen conjugate system.

* * * * *